(12) United States Patent
Akira et al.

(10) Patent No.: US 9,732,107 B2
(45) Date of Patent: Aug. 15, 2017

(54) METHOD FOR PRODUCING BETA-HEMATIN CRYSTAL COMPRISING STEP OF HEATING

(71) Applicants: OSAKA UNIVERSITY, Suita-shi, Osaka (JP); NIPPON ZENYAKU KOGYO CO., LTD., Sasagawa, Asaka-machi (JP)

(72) Inventors: Shizuo Akira, Osaka (JP); Ken Ishii, Osaka (JP); Cevayir Coban, Osaka (JP); Yoshikatsu Igari, Fukushima (JP); Yasumasa Kano, Fukushima (JP); Akina Otsuki, Fukushima (JP)

(73) Assignees: Osaka University, Osaka (JP); Nippon Zenyaku Kogyo Co., Ltd., Fukushima (JP)

( * ) Notice: Subject to any disclaimer, the term of this patent is extended or adjusted under 35 U.S.C. 154(b) by 0 days.

(21) Appl. No.: 14/895,314

(22) PCT Filed: Jun. 4, 2014

(86) PCT No.: PCT/JP2014/065396
§ 371 (c)(1),
(2) Date: Dec. 2, 2015

(87) PCT Pub. No.: WO2014/196657
PCT Pub. Date: Dec. 11, 2014

(65) Prior Publication Data
US 2016/0122378 A1 May 5, 2016

(30) Foreign Application Priority Data

Jun. 4, 2013 (JP) .................... 2013-118216

(51) Int. Cl.
*C07D 487/22* (2006.01)
*C07F 15/02* (2006.01)
*A61K 39/39* (2006.01)

(52) U.S. Cl.
CPC ............ *C07F 15/025* (2013.01); *A61K 39/39* (2013.01); *C07D 487/22* (2013.01); *C07B 2200/13* (2013.01)

(58) Field of Classification Search
CPC .................................................. C07D 487/22
See application file for complete search history.

(56) References Cited

U.S. PATENT DOCUMENTS

| 5,849,307 A | 12/1998 | Metz et al. |
| 2009/0041808 A1 | 2/2009 | Akira et al. |
| 2010/0111981 A1 | 5/2010 | Bohle et al. |
| 2010/0247568 A1 | 9/2010 | Tsukui et al. |
| 2013/0034731 A1 | 2/2013 | Akira et al. |

FOREIGN PATENT DOCUMENTS

| WO | WO 2006/061965 A1 | 12/2004 |
| WO | WO 2007/147255 A1 | 12/2007 |
| WO | WO 2009/057763 A1 | 5/2009 |
| WO | WO 2011/074711 A1 | 6/2011 |
| WO | WO 2012/012800 A2 | 1/2012 |

OTHER PUBLICATIONS

International Search Report dated Jul. 22, 2014, in PCT/JP2014/065396.
Coban at al., "Purified Malaria Pigment (Hemozoin) Enhances Dendritic Cell Maturation and Modulates the Isotype of Antibodies Induced by a DNA Vaccine," Infection and Immunity, Jul. 2002, 70(7):3939-3943.
Coban et al., "Toll-like receptor 9 mediates innate immune activation by the malaria pigment hemozoin," The Journal of Experimental Medicine, Jan. 3, 2005, 201(1):19-25.
Slater et al., "An iron-carboxylate bond links the heme units of malaria pigment," Proc. Natl. Acad. Sci. USA, Jan. 1991, 88:325-329.
Supplementary European Search Report dated Sep. 27, 2016, in EP 14808301.7.
Bohle et al., "Phase homogeneity and crystal morphology of the malaria pigment β-hematin," Acta Crystallographica, Oct. 1, 2002, D58(10:1):1752-1756.
Coban et al., "The Malarial Metabolite Hemozoin and Its Potential Use as a Vaccine Adjuvant," Allergology International, Jun. 1, 2010, 59(2):115-124.

*Primary Examiner* — Brian McDowell
(74) *Attorney, Agent, or Firm* — Foley & Lardner LLP

(57) ABSTRACT

This invention provides a method of preparing a β-hematin crystal comprising a step of heating, the β-hematin crystal obtained by such method, and a vaccine adjuvant composition containing the β-hematin crystal. The β-hematin crystal has a needle-like morphology, it has an average particle size of 0.6 to 1.2 μm, and it exhibits main peaks characteristics for angles of diffraction (2θ) of 7.4°, 12.2°, 21.6°, and 24.1° in an X-ray diffraction pattern obtained by powder X-ray diffractometry with Cu—Kα rays (with each peak including a plus-minus 0.2° diffraction angle).

5 Claims, 22 Drawing Sheets

Fig. 5

| | Heat | Usual (pellet) | Usual-sup | Usual-AC |
|---|---|---|---|---|
| Response rate for starting material | >95% | 50 to 60% | | |
| Recovery rate via centrifugation | 90 to 98% | 10 to 30% | 10 to 20% | - |
| Remaining hemin | <2% | 20 to 30% | About 10% | About 10% |
| Color | Grayish-brown to black | Reddish-brown to black | | |
| Maximal primary particle size | 0.5 to 5 μm | 0.2 to 0.8 μm | 0.1 to 0.5 μm | 0.3 to 2 μm |
| Particle size distribution — Range | 0.2 to 5 μm | 1 to 50 μm | 0.05 to 2 μm | 0.05 to 1 μm |
| Particle size distribution — Median size | 0.6 to 1.2 μm | 5 to 15 μm | 0.1 to 0.6 μm | 0.1 to 0.5 μm |
| Adjuvant effects (mouse OVA-tIgG) | Heat ≧ Usuals | Lower than Sup,AC | Higher than pellet | Higher than pellet |

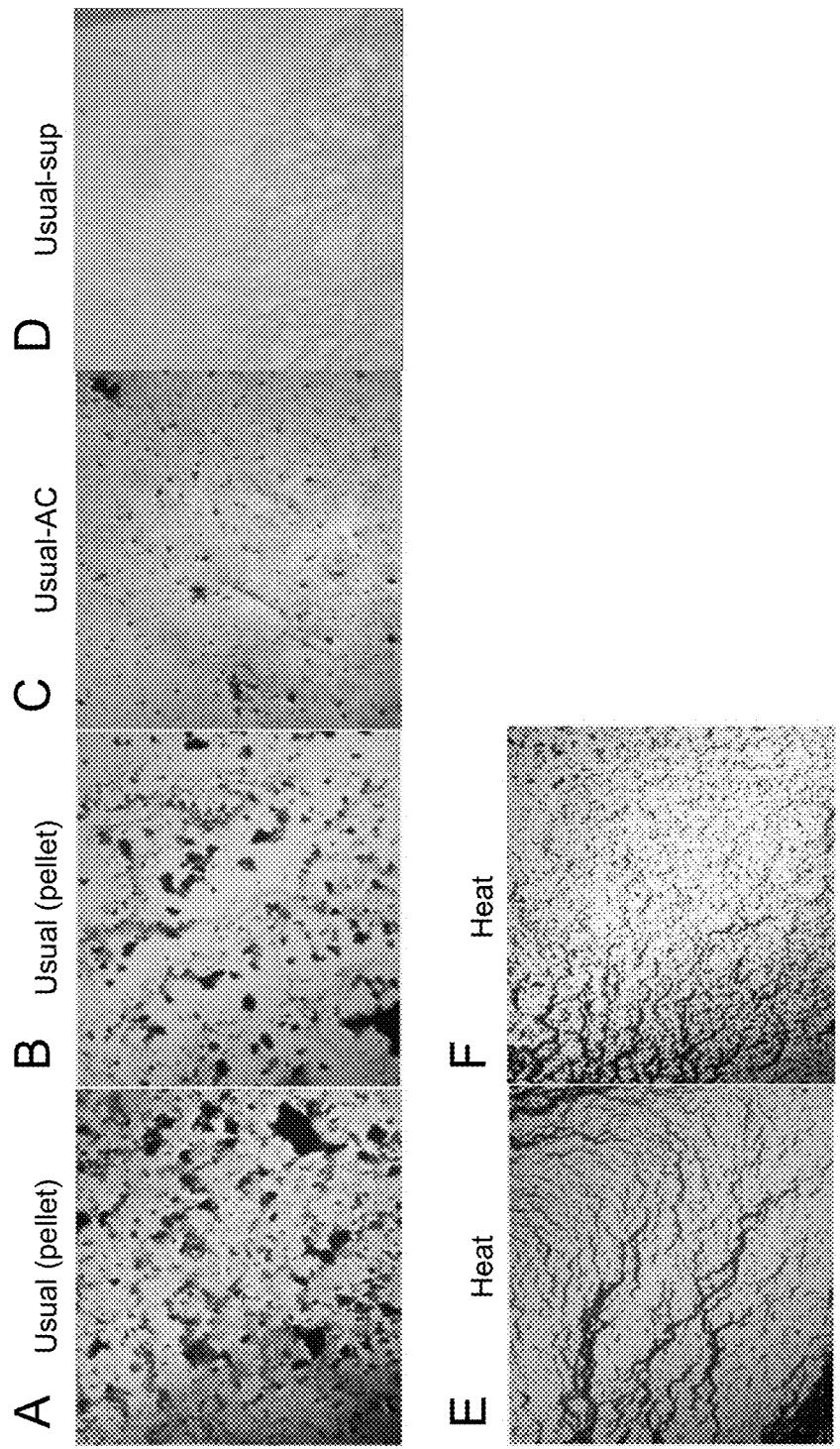

METHOD FOR PRODUCING BETA-HEMATIN CRYSTAL COMPRISING STEP OF HEATING

CROSS-REFERENCE TO RELATED APPLICATIONS

This application is a National Stage application of PCT/JP2014/065396, filed Jun. 4, 2014, which claims priority from Japanese application JP 2013-118216, filed Jun. 4, 2013.

TECHNICAL FIELD

The present invention relates to a method for producing β-hematin comprising a step of heating.

BACKGROUND ART

Hemozoin is a hydrophobic hem polymer, which is the detoxification product of the hem molecules found in the food vacuole of *Plasmodium protozoa*, and it can be produced by digestion of host hemoglobin by *Plasmodium protozoa*. As with CpG DNA, hemozoin acts as a ligand of Toll-like receptor 9. It is reported that the Toll-like receptor 9 is involved in innate immune responses to various pathogens, including *Plasmodium*. In other words, the immune system is activated in a MyD88-dependent manner when Toll-like receptor 9 recognizes a ligand.

The hemozoin synthesized from hemin chloride is referred to as "β-hematin" (see Slater et al., Proc. Natl. Acad., Sci., U.S.A., 88: 325-329, 1991).

It is reported that hemozoin activates spleen cells and dendritic cells of mice in vitro (see WO 2006/061965). It is also reported that hemozoin has adjuvant effects on the antibody production of ribonuclease A in mice (see U.S. Pat. No. 5,849,307).

In addition, it is reported that β-hematin has effects as an adjuvant of DNA vaccines (see Infect. Immun., July 2002; 70 (7): 3939-43). It is also reported that β-hematin functions as a ligand other than the TLR9 DNA molecule (a non-methylated DNA chain referred to as a so-called "CpG motif") (see J. Exp. Med., Jan. 3, 2005; 201 (1): 19-25).

In addition, a vaccine adjuvant used in combination with an allergen vaccine containing β-hematin has been reported (see WO 2009/057763), in which hemin chloride is dissolved in a sodium hydroxide solution, a small amount of hydrochloric acid is added thereto, acetic acid is added at 60° C., so as to adjust the pH level to around 4.8, and the resultant is allowed to stand at room temperature overnight. Subsequently, a precipitate is obtained via centrifugation, and a weakly-basic sodium bicarbonate solution (pH: about 9), 2% of which is sodium dodecyl sulfate (SDS), is added to the precipitate, followed by washing for replacement with water. The resultant is then centrifuged for fractionation, and a fraction with an average particle size of 50 to 200 nm has potent adjuvant effects (see WO 2011/074711).

SUMMARY OF THE INVENTION

The present invention provides a method for preparing a β-hematin crystal through a step of heating, a β-hematin crystal obtained by such method, and a vaccine adjuvant composition containing such β-hematin crystal.

The present inventors have previously developed vaccine adjuvant compositions containing β-hematin crystals (WO 2009/057763 and WO 2011/074711).

The present inventors conducted concentrated studies in order to develop a method for preparing a β-hematin crystal exhibiting higher adjuvant effects at a higher yield. As a result, they discovered that a β-hematin crystal exhibiting more potent adjuvant effects and higher crystallinity than the resultant obtained by the conventional method could be produced from hemin chloride as a starting material by employing a method comprising a step of heating at 90° C. or higher for 30 minutes or longer, and preferably 80° C. to 90° C. for 1 hour or longer. They also discovered that production yield could be improved, thereby completing the present invention.

Specifically, the present invention is described as follows.

[1] A β-hematin crystal having a needle-like morphology, having an average particle size of 0.6 to 1.2 μm, and exhibiting main peaks characteristics for angles of diffraction (2θ) of 7.4°, 12.2°, 21.6°, and 24.1° in an X-ray diffraction pattern obtained by powder X-ray diffractometry with Cu—Kα rays, wherein each peak includes a plus-minus 0.2° diffraction angle.

[2] The β-hematin crystal according to [1], wherein OH— or OH2 is bound to the sixth coordination position.

[3] A β-hematin crystal having at least one of the structural features (i) to (v) below:
(i) solid-state $^1$H-NMR analysis demonstrates main peaks at 6.8 ppm and −1.4 ppm;
(ii) electron spin resonance (ESR) analysis at room temperature results in the detection of two apparent signals at around 0 to 200 mT (g=6.122) and at around 200 to 400 mT (g=2.005), ESR analysis at −50° C. results in the detection of a signal at around 0 to 100 mT that is stronger than a signal at around 200 to 300 mT, and ESR analysis at −150° C. results in the detection of a signal at around 0 to 100 mT that is at least twice as strong as a signal at around 200 to 300 mT;
(iii) near-infrared spectroscopy does not result in the detection of peaks at 4440 cm$^{-1}$, 5780 cm$^{-1}$, and 5960 cm$^{-1}$,
(iv) ultraviolet-visible spectroscopy results in the detection of peaks at 493 nm and 670 nm; and
(v) thermogravimetric/differential thermal analysis results in the detection of, in the air, thermacogenesis at around 250° C. and rapid oxidative decomposition up to 400° C. and, in nitrogen, thermal decomposition involving endothermic changes at 360° C. and 440° C. and thermal decomposition involving thermacogenesis at around 700° C.

[4] A vaccine adjuvant composition comprising the β-hematin crystal according to any of [1] to [3].

[5] A method for producing β-hematin comprising adding an HCl aqueous solution to a solution of hemin chloride dissolved in an NaOH aqueous solution, adding acetic acid dropwise thereto so as to adjust the pH level to 4 to 6, and heating the resulting mixture to 80° C. or higher.

[6] The method for producing β-hematin according to [5], wherein heating is carried out for 30 minutes or longer.

[7] The method for producing β-hematin according to [5] or [6], wherein the yield determined via thin-layer chromatography is 90% or higher in accordance with the formula: [molar quantity of starting material]/[molar quantity of β-hematin×2]×100.

[8] A β-hematin crystal produced by the method according to any of [5] to [7].

[9] The β-hematin crystal according to [8], which exhibits greater main peak intensity characteristics for angles of diffraction (2θ) of 7.4°, 12.2°, 21.6°, and 24.1° in an X-ray diffraction pattern obtained by powder X-ray diffractometry with Cu—Kα rays and higher crystallinity than a second βhematin crystal, which is obtained by dissolving hemin chloride in an NaOH aqueous solution, adding a small quantity of hydrochloric acid thereto, adding acetic acid dropwise thereto at 60° C. so as to adjust the pH level to 4 to 6, allowing the mixture to stand at room temperature overnight without heating, subjecting the mixture to centrifugation, and washing the resultant with an SDS-containing weakly basic solution with a pH of about 9.

[10] The β-hematin crystal according to [8] or [9], wherein OH— or OH2 is bound to the sixth coordination position.

[11] The β-hematin crystal according to any of [8] to [10], which further has at least one of the structural features (i) to (vi) below:

(i) solid-state $^1$H-NMR analysis demonstrates main peaks at 6.8 ppm and −1.4 ppm;

(ii) electron spin resonance (ESR) analysis at room temperature results in the detection of two apparent signals at around 0 to 200 mT (g=6.122) and at around 200 to 400 mT (g=2.005), ESR analysis at −50° C. results in the detection of a signal at around 0 to 100 mT that is stronger than a signal at around 200 to 300 mT, ESR analysis at −150° C. results in the detection of a signal at around 0 to 100 mT that is at least twice as strong as a signal at around 200 to 300 mT, and the integral of the signals appearing at around 200 to 400 mT is 1/10 or lower than that of a second β-hematin crystal, which is obtained by dissolving hemin chloride in an NaOH aqueous solution, adding a small quantity of hydrochloric acid thereto, adding acetic acid dropwise thereto at 60° C. so as to adjust the pH level to 4 to 6, allowing the mixture to stand at room temperature overnight without heating, subjecting the mixture to centrifugation, and washing the resultant with an SDS-containing weakly basic solution with a pH of about 9;

(iii) near-infrared spectroscopy does not result in the detection of peaks at 4440 cm$^{-1}$, 5780 cm$^{-1}$, and 5960 cm$^{-1}$, (iv) ultraviolet-visible spectroscopy results in the detection of peaks at 493 nm and 670 nm;

(iv) ultraviolet-visible spectroscopy results in the detection of peaks at 493 nm and 670 nm;

(v) thermogravimetric/differential thermal analysis results in the detection of, in the air, thermacogenesis at around 250° C. and rapid oxidative decomposition up to 400° C. and, in nitrogen, thermal decomposition involving endothermic changes at 360° C. and 440° C. and thermal decomposition involving thermacogenesis at around 700° C. in nitrogen; and (vi) when compared with a second β-hematin crystal obtained by dissolving hemin chloride in an NaOH aqueous solution, adding a small quantity of hydrochloric acid thereto, adding acetic acid dropwise thereto at 60° C. so as to adjust the pH level to 4 to 6, allowing the mixture to stand at room temperature overnight without heating, subjecting the mixture to centrifugation, and washing the resultant with an SDS-containing weakly basic solution with a pH of about 9 via Raman spectroscopic analysis, the β-hematin crystal exhibits substantially the same peak intensities at 1567 cm$^{-1}$ and at 1370 cm$^{-1}$ unlike the second β-hematin crystal that exhibits an intensity ratio of the peak at 1375 cm$^{-1}$ to the peak at 1568 cm$^{-1}$ of 0.75:1 to 0.85:1 in the spectrum obtained at an excitation wavelength of 514.4 nm, and the β-hematin crystal exhibits substantially the same peak intensities at 1625 cm$^{-1}$ and at 370 cm$^{-1}$ unlike the second β-hematin crystal that exhibits an intensity ratio of the peak at 370 cm$^{-1}$ to the peak at 1625 cm$^{-1}$ of 0.45:1 to 0.55:1 in the spectrum obtained at an excitation wavelength of 1064 nm.

[12] The β-hematin crystal according to any of [8] to [11], which further exhibits properties (a) to (d) when compared with a second β-hematin crystal obtained by dissolving hemin chloride in an NaOH aqueous solution, adding a small quantity of hydrochloric acid thereto, adding acetic acid dropwise thereto at 60° C. so as to adjust the pH level to 4 to 6, allowing the mixture to stand at room temperature overnight without heating, subjecting the mixture to centrifugation, and washing the resultant with an SDS-containing weakly basic solution with a pH of about 9:

(a) while the color of a suspension of the second β-hematin crystal is reddish-brown to black, that of the β-hematin crystal is grayish-brown to black;

(b) infrared spectrometry (IR) analysis demonstrates higher crystal density and a higher proportion of single crystals than the second β-hematin crystal;

(c) X-ray diffraction analysis demonstrates crystallite size greater than that of the second β-hematin crystal; and (d) thermogravimetric/differential thermal analysis demonstrates lower rates of impurities or particles with different crystal forms (or amorphous particles) than the second β-hematin crystal.

A vaccine adjuvant composition containing the β-hematin crystal according to any of [8] to [12].

The β-hematin crystal according to the present invention can be produced by a method comprising a step of heating using hemin chloride as a starting material. In comparison with conventional methods of β-hematin synthesis, the β-hematin crystal can be synthesized within a shorter period of time with a higher yield. In addition, the vaccine adjuvant composition containing the β-hematin crystal of the present invention exerts higher adjuvant effects than β-hematin crystals obtained by conventional techniques. The vaccine adjuvant composition containing the β-hematin crystal produced by the method of the present invention may be used in combination with an allergen vaccine or an infection vaccine for pathogens such as bacteria, viruses, rickettsiae, or parasites, the antibody titer for such pathogens is elevated in vivo, and allergic diseases and infectious diseases can be prevented or treated more effectively, compared with cases in which an adjuvant is not used in combination.

This description includes part or all of the content as disclosed in the description and/or drawings of Japanese Patent Application No. 2013-118216, which is a priority document of the present application.

BRIEF DESCRIPTION OF THE DRAWINGS

FIG. 5 shows response rates for starting materials, recovery rates via centrifugation, rates of remaining hemin chloride, color of β-hematin obtained, the maximal primary particle size of β-hematin, and the particle size distribution thereof, in accordance with the Heat method and the Usual method.

FIG. 6 shows microscopic images of β-hematin synthesized by the Heat method and the Usual method.

EMBODIMENTS FOR CARRYING OUT THE INVENTION

Figure 1:
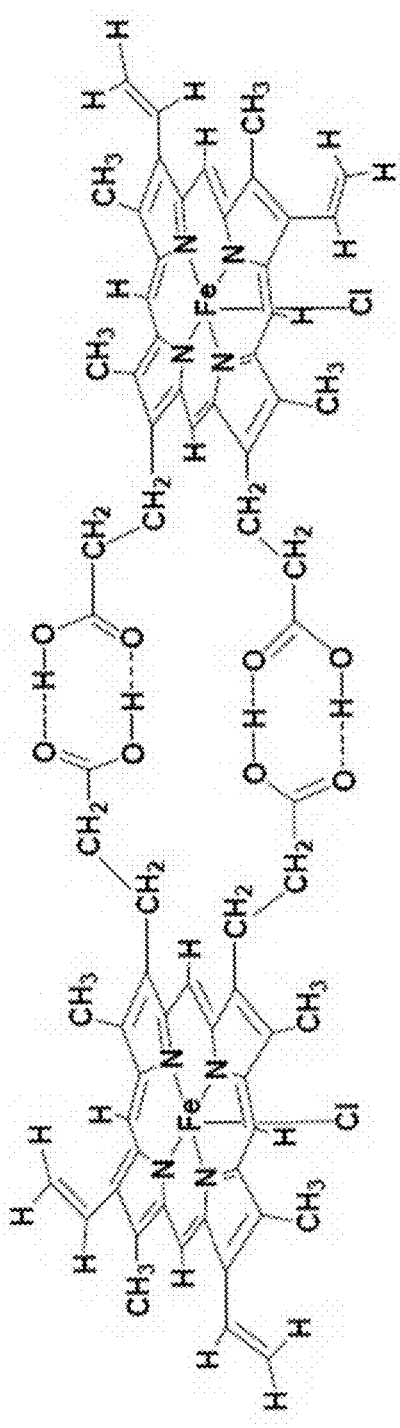
FIG. 1 shows the structure of hemin chloride.
Figure 2:
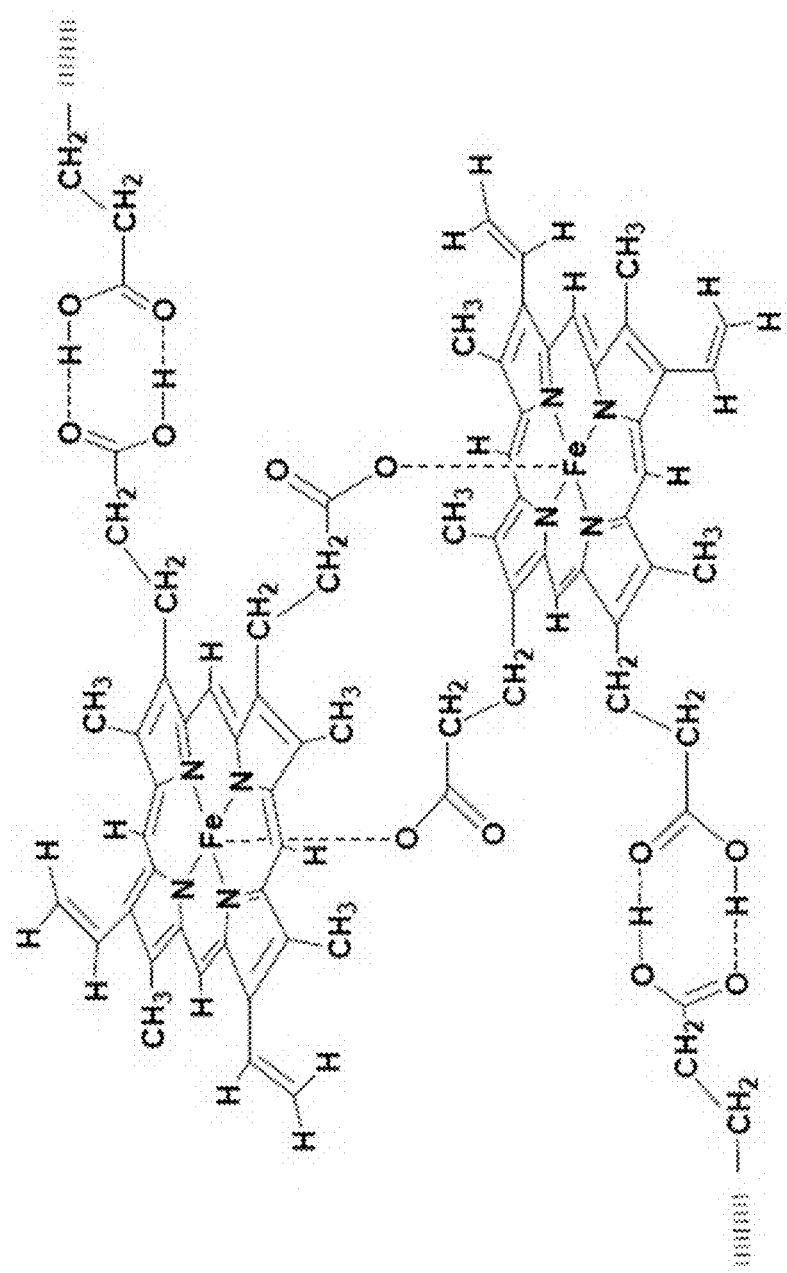
FIG. 2 shows the structure of β-hematin.

Hereafter, the present invention is described in detail. β-Hematin βHT), which is a constituent of the vaccine adjuvant composition according to the present invention, is synthetic hemozoin, and it is a hemin dimer crystal that can be synthesized from hemin chloride in the manner described below. For example, commercially available hemin chloride purified from porcine blood can be used. FIG. 1 shows the structure of hemin chloride and FIG. 2 shows the structure of β-hematin.

Hemin chloride (100 mg) is dissolved in 10 ml of a 1 N NaOH aqueous solution, and 1 ml of a 1 N HCl aqueous solution is added thereto. In addition, acetic acid is added dropwise thereto, so as to adjust the pH level to 4 to 6, and preferably 4.5 to 4.8. Subsequently, a mixture containing hemin chloride is heated to 90° C. or higher for 30 minutes or longer, and preferably to 80° C. to 90° C. for 1 hour or longer. Following the heating, the resultant is washed by centrifugation once in an aqueous solution of disodium phosphate with a pH of 7.5 to 9.5, and preferably of 9.0, and to washing by centrifugation 3 or 4 times with the use of purified water for replacement. Thus, β-hematin can be obtained in the form of a crystal. The resulting β-hematin can be sterilized using an autoclave (121° C., 20 minutes).

Figure 3:
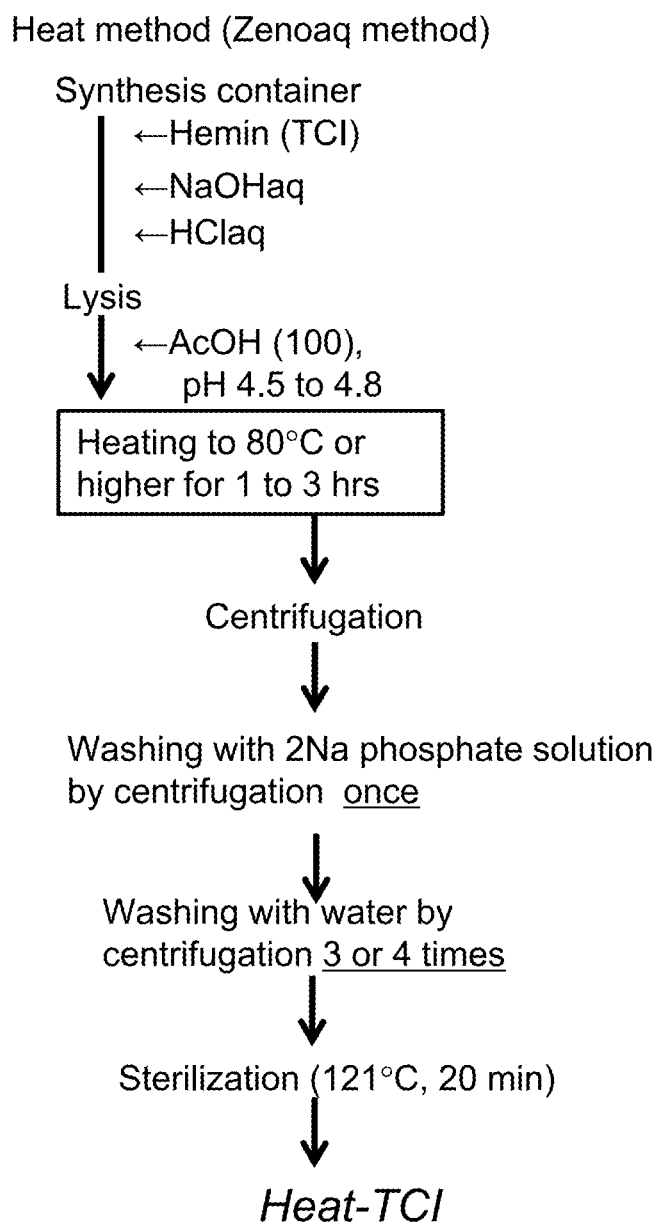
FIG. 3 shows a procedure for the Heat method, which is the method for β-hematin synthesis according to the present invention.

The method for producing β-hematin according to the present invention described above is referred to as the Heat method. FIG. 3 shows a procedure for the Heat method.

According to a conventional technique (i.e., the Usual method), β-hematin was produced by the method described below.

Hemin chloride (45 mg) is dissolved in 4.5 ml of a 1 N NaOH aqueous solution, and 0.45 ml of a 1 N HCl aqueous solution is added thereto. Acetic acid is added dropwise to the resulting solution at room temperature to 70° C., and preferably at 40° C. to 60° C., so as to adjust the pH level to 4 to 6, preferably 4.5 to 5, and more preferably 4.8. The mixture is allowed to stand at room temperature overnight or at room temperature to 40° C. for 1 to 5 hours, the mixture is subjected to centrifugation, the resultant is washed by centrifugation three times with a weakly basic solution containing 2% SDS with a pH of about 9, such as a 0.1M sodium bicarbonate buffer (pH 9.1), and the resultant is then washed by centrifugation 6 to 8 times with purified water for replacement therewith. Both the supernatant and the precipitate resulting from centrifugation with purified water contain β-hematin.

Figure 4:
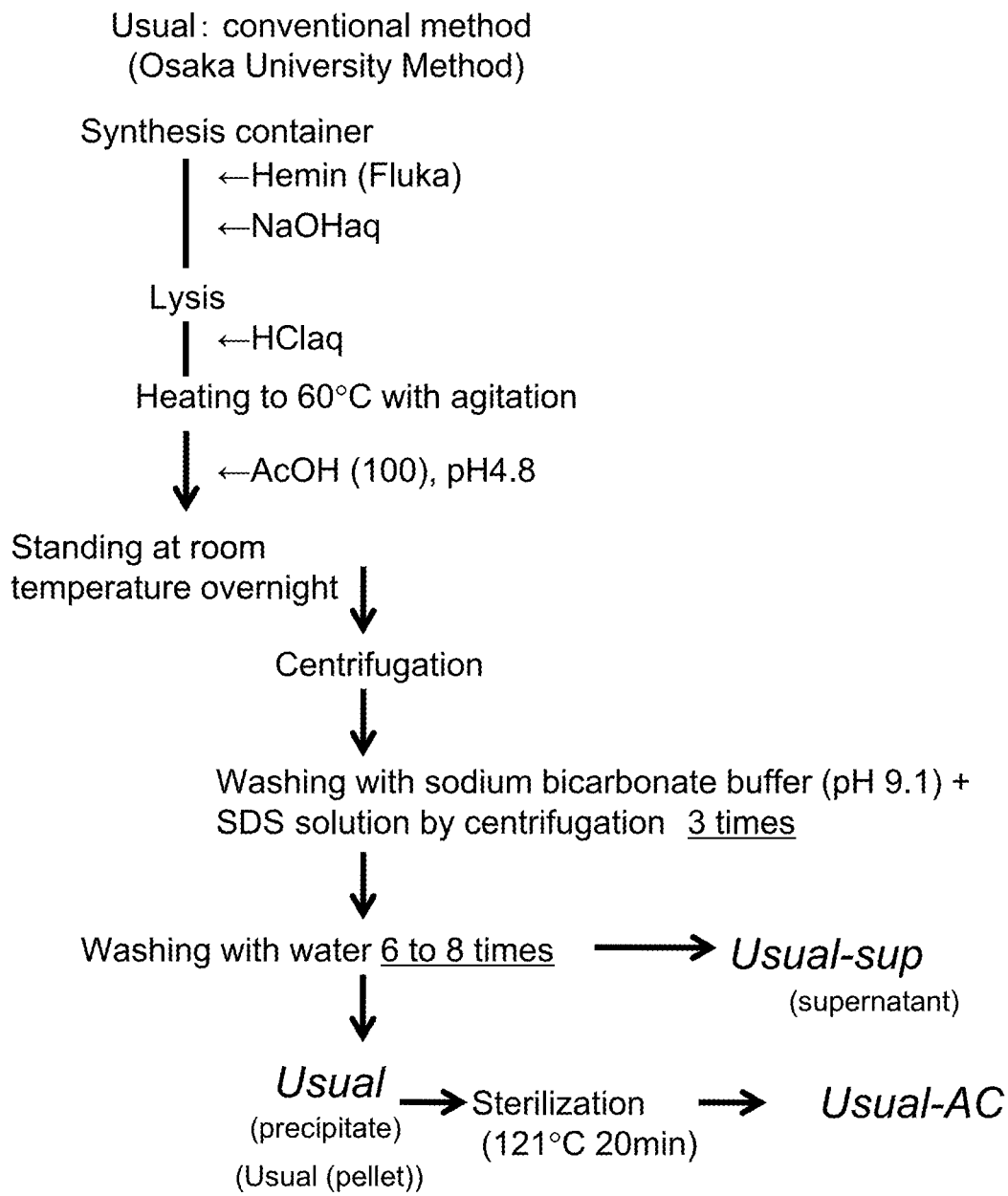
FIG. 4 shows a procedure for the Usual method, which is a conventional method for β-hematin synthesis.

FIG. 4 shows a procedure for the Usual method. In the Usual method, as shown in FIG. 4, properties of the supernatant (referred to as "Usual-sup"), the precipitate (referred to as "Usual (pellet)") resulting from centrifugation with purified water, and the product obtained via sterilization of the precipitate using an autoclave (121° C. for 20 minutes) (referred to as "Usual-AC") were examined.

The synthesized β-hematin can be quantified by dissolving the same in 0.1 M sodium chloride containing 2% SDS, allowing the solution to stand at room temperature for 2 hours, and measuring the absorbance at 400 nm. Quantification can be carried out in accordance with the method described in, for example, Proc. Natl. Acad. Sci., U.S.A., 93: 11865-11870, 1996.

β-Hematin produced by the Heat method according to the present invention has the properties described below.

FIG. 5 shows response rates for starting materials in accordance with the Heat method and the Usual method, recovery rates via centrifugation, rates of remaining hemin chloride, color of β-hematin obtained, the maximal primary particle size, and the particle size distribution of the β-hematin.

While the response rate for starting materials is 50% to 60% in accordance with the conventional Usual method, the response rate exceeds 95% in accordance with the Heat method of the present invention. While the precipitate yield is 10% to 30 in accordance with the Usual method (Usual (Pellet)), the yield exceeds 90% in accordance with the Heat method. The response rate can be determined by separating β-hematin via thin-layer chromatography on the basis of the size and the density of chromatography spots. The yield (%) can be determined in accordance with the formula: [molar quantity of starting material]/[molar quantity of βHT×2]× 100.

β-Hematin according to the present invention is in the form of a crystal with a needle-like morphology, and the maximal primary particle size is 0.5 to 5 μm. The term "primary particle" refers to a unit particle that has not undergone aggregation and cannot disperse any further. The particle size range is found to be 0.5 to 5 μm through particle size distribution measurement, and the median size (average particle size) is 0.6 to 1.2 μm. Particle size distribution can be determined with the use of, for example, a wet laser diffraction/scattering particle size distribution measuring apparatus.

As shown in FIG. 5, the maximal primary particle size of β-hematin produced by the Heat method is somewhat greater than that of β-hematin produced by the conventional Usual method. The maximal primary particle size is equivalent to the length of a needle-like or rod-like particle observed via SEM.

The color of the β-hematin suspension was grayish-brown to black. In contrast, the color of the β-hematin suspension obtained by the Usual method was reddish-brown to black. Such difference in color is considered to reflect the difference in crystallinity between the β-hematin produced by the Heat method and the β-hematin produced by the Usual method.

Properties of the β-hematin produced by the Heat method according to the present invention determined via structural analysis by means of infrared spectrometry (IR), X-ray diffraction analysis, solid-state $^1$H-NMR analysis, Raman spectrometry, electron spin resonance (ESR) analysis at room temperature, near-infrared spectrometry (NIR), ultraviolet-visible spectroscopy (UV-vis), and thermogravimetric/differential thermal analysis (TG-DTA) are as described below. Such properties are described in comparison with those of the β-hematin obtained by the Usual method.

Properties Determined Via Infrared Spectrometry (IR)

The β-hematin produced by the Heat method exhibits main peaks characteristic for 1710 cm$^{-1}$, 1662 cm$^{-1}$, 1297 cm$^{-1}$, 1280 cm$^{-1}$, 1209 cm$^{-1}$, 939 cm$^{-1}$, and 714 cm$^{-1}$ (with each peak including wave number shifts within ±2 cm$^{-1}$). While the β-hematin produced by the Usual method shows similar peaks and it has substantially the same primary structure, the peak width of the main absorption band of the β-hematin produced by the Heat method is observed to be sharper. That is, it has so-called high crystallinity because of higher crystal density and higher single crystal proportion.

In the case of the β-hematin produced by the Usual method, peaks are detected in a broad range, including from 1,600 cm$^{-1}$ to 1,500 cm$^{-1}$ and 1,420 cm$^{-1}$ to 1,350 cm$^{-1}$. This indicates that large quantities of carboxylic acids or carboxylates other than Fe—COO bonds are present. In the case of the β-hematin produced by the Heat method, broad peaks are not observed at around 1,600 cm$^{-1}$ to 1,500 cm$^{-1}$ or 1,420 cm$^{-1}$ to 1,350 cm$^{-1}$. That is, the abundance of carboxylic acids or carboxylates other than Fe—COO bonds in the β-hematin crystal produced by the Heat method is lesser than that in the β-hematin crystal produced by the Usual method.

Properties Determined Via X-Ray Diffraction Analysis

The β-hematin crystal produced by the Heat method exhibits main peaks characteristics for angles of diffraction (2θ) of 7.4°, 12.2°, 21.6°, and 24.1° observed in an X-ray diffraction pattern obtained by powder X-ray diffractometry with Cu—Kα rays (with each peak including a plus-minus 0.2° of the diffraction angle). While the β-hematin crystal produced by the Usual method exhibits similar peaks, the peak intensity of the β-hematin crystal produced by the Heat method is stronger.

As a result of X-ray diffraction analysis, the β-hematin produced by the Heat method is found to have a greater crystallite size and a higher degree of crystallinity than the β-hematin produced by the Usual method, although the crystal forms are substantially the same.

Properties Determined Via Solid-State $^1$H-NMR Analysis

The β-hematin crystal produced by the Heat method exhibits main peaks at 6.8 ppm and −1.4 ppm, and the β-hematin crystal produced by the Usual method exhibits main peaks at 6.5 ppm and −4.0 ppm. While spectral separation and identification are difficult due to the magnetic properties of iron, such β-hematin crystals exhibit different spectral configurations. Such results indicate that there is a structural difference in, for example, hexacoordination of an iron atom, which is not observed via IR analysis.

Properties Determined Via Raman Spectrometry

The β-hematin crystal produced by the Heat method and the β-hematin crystal produced by the Usual method are found to exhibit substantially the same peaks via Raman spectrometry at excitation wavelengths of 514.4 nm and 1064 nm. The intensity ratios of peaks in accordance with the Heat method differ from those in accordance with the Usual method. According to the spectra at the excitation wavelength of 514.4 nm, specifically, the peak intensity ratio at 1375 cm$^{-1}$ relative to the peak intensity at 1568 cm$^{-1}$ is 0.75 to 0.85 when the Usual method is employed. In contrast, the peak intensity at 1567 cm$^{-1}$ is substantially the same as the peak intensity at 1370 cm$^{-1}$ when the Heat method is employed. According to the spectra at the excitation wavelength of 1064 nm, the peak intensity ratio at 370 cm$^{-1}$ relative to the peak intensity at 1625 cm$^{-1}$ is 0.45 to 0.55 in the case of the β-hematin produced by the Usual method. In contrast, the peak intensity at 370 cm$^{-1}$ is substantially the same as the peak intensity at 1625 cm$^{-1}$ in the case of the β-hematin produced by the Heat method. This indicates that there are differences in the state of coordination to iron atoms and the crystalline state.

Properties Determined Via Electron Spin Resonance (ESR) Analysis at Room Temperature According to ESR analysis conducted at room temperature, the β-hematin crystal produced by the Heat method exhibits two apparent signals at around 0 to 200 mT (g=6.122) and at around 200 to 400 mT (g=2.005). The term "room temperature" used herein indicates 1° C. to 30° C., and preferably 20° C. to 30° C. The β-hematin produced by the Usual method exhibits substantially no signals at around 0 to 200 mT in the lower magnetic field. Also, there are differences in the signal intensity absolute values, and the β-hematin produced by the Usual method exhibits the integral of signals appearing in a broad range at around 200 to 400 mT, which is approximately 13 times stronger than that exhibited by the β-hematin produced by the Heat method. Specifically, the β-hematin produced by the Heat method exhibits the integral of signals appearing in a broad range at around 200 to 400 mT, which is 1/10 or less, and preferably about 1/13, of the figure for the β-hematin crystal produced by the Usual method.

When the measurement temperature was changed from room temperature to −50° C. and −150° C., the β-hematin produced by the Usual method exhibited a slight change in the lower magnetic field (around 0 to 100 mT), and the β-hematin produced by the Heat method exhibited a significantly elevated signal in the higher magnetic field (around 200 to 300 mT), when measurement was carried out at −50° C. Specifically, the signal detected at around 0 to 100 mT was found to be stronger than the signal detected at around 200 to 300 mT as a result of ESR analysis conducted at −50° C., and such difference became apparent at −150° C. The β-hematin produced by the Usual method exhibited no change in the higher magnetic field (around 200 to 300 mT) and elevation in the lower magnetic field (around 0 to 100 mT). In contrast, the β-hematin produced by the Heat method exhibited elevation in the lower magnetic field (around 0 to 100 mT) and a lowered signal in the higher magnetic field (around 200 to 300 mT). That is, the signal detected at around 0 to 100 mT was found to be at least twice as strong as the signal detected at around 200 to 300 mT as a result of ESR analysis at −150° C.

The results demonstrate that significant differences exist in terms of paramagnetic species types and densities. While the β-hematin produced by the Usual method exhibits a low-spin state for trivalent iron, the β-hematin produced by the Heat method exhibits a lower signal intensity than the β-hematin produced by the Usual method. In addition, the β-hematin produced by the Heat method exhibits complicated spectra involving a low-spin state and a high-spin state. Such phenomena are considered to result from different states of coordination to iron atoms and different interactions between iron atoms.

Properties Determined Via Near-Infrared Spectrometry

In the near-infrared spectra concerning the β-hematin crystal produced by the Heat method, a reduction was observed in the reflection of the entire wavelength region in comparison with the spectra concerning the β-hematin produced by the Usual method. In addition, peaks at 4440 $cm^{-1}$, 5780 $cm^{-1}$, and 5960 $cm^{-1}$ observed in the β-hematin produced by the Usual method were not substantially observed in the β-hematin produced by the Heat method. This is considered to result from changes in OH and CH. In addition, differences in the spectral configuration as a whole lead to differences in configuration, such as in relation to crystalline structure and particle size.

Properties Determined Via Ultraviolet-Visible Spectroscopy

The β-hematin crystal produced by the Heat method exhibited spectra with peaks at 493 nm and 670 nm, and small differences in absorbance from 200 nm to 1000 nm are discerned via ultraviolet-visible spectroscopy, which was conducted by dispersing particles in water. The β-hematin crystal produced by the Usual method exhibited spectra with peaks at 368 nm, 436 nm, and 645 nm and strong absorption from 300 nm to 500 nm.

The results demonstrate that colors differ from each other and that there are differences in terms of molecular structures and crystalline structures.

Properties Determined Via Thermogravimetric/Differential Thermal Analysis

According to thermogravimetric/differential thermal analysis, the β-hematin crystal produced by the Heat method undergoes thermacogenesis at around 250° C. and rapid oxidative decomposition up to 400° C. in the air. Such β-hematin crystal undergoes thermal decomposition involving endothermic changes at around 360° C. and 440° C. and thermal decomposition involving thermacogenesis at around 700° C. in nitrogen. The behavior of the β-hematin crystal produced by the Usual method determined via TG-DTA analysis is substantially the same as that of the β-hematin produced by the Heat method. However, oxidative decomposition continues at two phases to around 500° C. in the air. In nitrogen, the first-phase thermal decomposition takes place at around 300° C., which is earlier than the β-hematin produced by the Heat method, and the reduction in weight because of decomposition at the second and subsequent phases is lower than that observed in the β-hematin produced by the Heat method.

The results demonstrate that the proportion of impurities or particles with different crystalline forms (or amorphous particles) in the β-hematin produced by the Usual method is greater than that observed in the β-hematin produced by the Heat method.

According to the analyses described above, in summary, the β-hematin crystal produced by the Heat method according to the present invention has a needle-like morphology, an average particle size of 0.6 to 1.2 μm, and main peaks characteristic for angles of diffraction (2θ) of 7.4°, 12.2°, 21.6°, and 24.1° as observed in the X-ray diffraction pattern obtained by powder X-ray diffractometry with Cu—Kα rays (with each peak including plus-minus 0.2° of the diffraction angle) and at least one of the properties selected from among (i) to (v) below:

(i) solid-state $^1$H-NMR analysis demonstrates main peaks at 6.8 ppm and −1.4 ppm;

(ii) electron spin resonance (ESR) analysis at room temperature results in the detection of two apparent signals at around 0 to 200 mT (g=6.122) and at around 200 to 400 mT (g=2.005), ESR analysis at −50° C. results in the detection of a signal at around 0 to 100 mT that is stronger than a signal at around 200 to 300 mT, and ESR analysis at −150° C. results in the detection of a signal at around 0 to 100 mT that is at least twice as strong as a signal at around 200 to 300 mT;

(iii) near-infrared spectroscopy does not result in the detection of peaks at 4440 $cm^{-1}$, 5780 $cm^{-1}$, and 5960 $cm^{-1}$;

(iv) ultraviolet-visible spectroscopy results in the detection of peaks at 493 nm and 670 nm; and (v) thermogravimetric/differential thermal analysis results in the detection of, in the air, thermacogenesis at around 250° C. and rapid oxidative decomposition up to 400° C. and, in nitrogen, thermal decomposition involving endothermic changes at 360° C. and 440° C. and thermal decomposition involving thermacogenesis at around 700° C.

The present invention provides a vaccine adjuvant composition containing an effective amount of the β-hematin in order to stimulate immune responses. When a vaccine adjuvant is used in combination with a vaccine, it enhances vaccine effects and increases the production of antibodies reacting with the immunogen used as a vaccine in vivo. The present invention also provides a vaccine composition including an allergen vaccine containing such vaccine adjuvant composition and allergens in an amount effective for stimulation of immune responses or a vaccine for use in infectious diseases containing antigens of pathogens such as bacteria, viruses, rickettsiae, or parasites.

The amount of β-hematin in a vaccine adjuvant composition and a vaccine composition is 5 μM to 3 mM, preferably 7.5 μM to 2 mM, more preferably 10 μM to 2 mM, still further preferably 10 μM to 1,000 μm, and still further more preferably 50 μM to 500 μM, when a substance that binds β-hematin to an antigen (e.g., aluminum hydroxide or Pullulan) is included.

When β-hematin is used alone as an adjuvant, the amount thereof is 50 μM to 30 mM, preferably 100 μM to 20 mM, more preferably 500 μM to 10 mM, further preferably 1 mM to 8 mM, and still further preferably 3 mM to 5 mM.

Freund's complete adjuvants, killed microorganisms (e.g., killed tubercle bacilli) and other immunostimulators (e.g., Alum adjuvant) may be added to the vaccine adjuvant composition of the present invention, in addition to β-hematin.

The adjuvant of the present invention can be used for an allergen vaccine and a vaccine for use in infectious diseases.

The allergen vaccine is a vaccine to block the action of IgE responsible for allergies by the production of IgG antibody against allergens or to increase type 1 helper T cells (Th1 cells) specific to allergens in vivo, thereby decreasing type 2 helper T cells (Th2 cells), which are involved in allergic symptoms, through introduction of allergens into organisms. Such allergen vaccine can suppress the allergic symptoms by desensitization. The allergen vaccine comprises allergens causing various kinds of allergies. Examples of allergens to be used in combination with the vaccine adjuvant composition of the present invention include, but are not limited to, allergens such as food allergens, house dust allergens, pollen allergens (e.g., cedar pollen), and animal hair. Specific examples of pollen allergens include cedar pollen allergens (Cry j1 and Cry j2), ragweed allergens (Amba1, Amba2, Amba5, Ambt5, and Ambp5), and *Dactylis glomerata* (orchard grass) allergens (Dacg2). Specific examples of food allergens include casein, lactalbumin, lactoglobulin, ovomucoid, ovoalbumin, and conalbumin. Specific examples of house dust allergens include mite allergens (Derf1, Derf2, Zen1, Derp1, and Derp2). Among these, cedar pollen allergens (e.g., Cry j1) and mite allergens (Zen1, Derf1, and Derf2) are particularly desirable.

Examples of the vaccines for use in infectious diseases include inactivated complete vaccine, subunit vaccine, and toxoid. These vaccines impart immunity against pathogens such as bacteria, viruses, rickettsiae, or parasites in animals.

When the β-hematin produced by the Heat method of the present invention is used as an adjuvant and an immunogen as a vaccine is administered to an animal, an antibody titer rapidly increases, a sufficient antibody titer is attained within 1 to 3 weeks after the vaccine administration, and the maximal antibody titer is attained in 8 to 10 weeks. In addition, a high antibody titer is maintained, and the antibody titer determined 10 weeks after the vaccine administration is maintained for 15 weeks or longer, preferably 20 weeks or longer, more preferably 30 weeks or longer, further preferably 40 weeks or longer, and particularly preferably 50 weeks or longer. When the β-hematin produced by the Heat method is used until the maximal antibody titer is attained and while a high antibody titer is maintained, the effects attained thereby are superior to those attained with the use of the β-hematin produced via the Usual method.

Examples of the vaccines for use in infectious diseases for humans include vaccines for infections with influenza (e.g., type A influenza, type A/H1N1 influenza, and type B influenza), poliovirus, Japanese encephalitis, tubercle bacillus, human papillomavirus, *Plasmodium falciparum*, SARS, avian influenza that may infect humans, typhoid, paratyphoid, black death, whooping cough, and epidemic typhus. Examples of the vaccines for use in infectious diseases for animals other than humans include those against equine influenza virus, equine herpes virus, equine encephalomyelitis virus, foot-and-mouth disease virus, rabies, feline panleukopenia, feline rhinotracheitis, infectious bovine rhinotracheitis, parainfluenza-3, bovine virus diarrhea, bovine adenovirus, porcine parvovirus, canine adenoviruses, canine distemper virus, canine parvovirus, canine parainfluenza, avian influenza, brucellosis, vibriosis, leptospirosis, clostridial infections, and salmonellosis. Among them, vaccines for infectious diseases against *Escherichia coli* (bovine mastitis), *Staphylococcus aureus* (bovine mastitis), *Mycoplasma* (porcine pneumonia), PRRS virus (porcine pneumonia), canine rabies virus, etc., are desirable.

In the present invention, the vaccine adjuvant composition comprising β-hematin may be used alone. In such case, the vaccine adjuvant composition and the above vaccine may be administered separately to animals. In addition, the vaccine adjuvant composition and the vaccine may be used in a mixed form. In such a case, a vaccine composition comprising β-hematin can be used.

Animals to which the vaccine adjuvant composition and the vaccine composition of the present invention are to be administered are not particularly limited, but are limited only to animals having immune systems, including mammals and birds. Examples of mammals include humans, monkeys, cows, horses, pigs, sheep, goats, dogs, cats, guinea pigs, rats, and mice. Examples of birds include chickens, ducks, and geese. The vaccine adjuvant composition and the vaccine composition according to the present invention are particularly useful as allergy vaccines and vaccines for use in infectious diseases for humans, allergy vaccines and vaccines for use in infectious diseases for pet animals such as dogs and cats, and vaccines for use in infectious diseases for industry animals such as cows, pigs, and chickens.

The amount of antigen in the vaccine composition may be varied depending on the kind of infections to be targeted and animal species to which it is to be administered, but it is usually in the range of several tens of nanograms to several milligrams per single instance of administration.

The vaccine adjuvant composition and the vaccine composition of the present invention may be in the form of an aqueous or non-aqueous sterilized solution, suspension, or emulsion. Moreover, such composition may comprise a pharmaceutically acceptable diluent, an auxiliary agent, and a carrier, etc., such as salt, buffer, etc. The vaccine compositions can be administered through various routes, such as oral, nasal, transmucosal, intramuscular, percutaneous, subcutaneous, intradermal, intranasal, or intratracheal routes. Also, the vaccine composition can be administered by means of, for example, instillation, aspiration, spray, or coating. The vaccine adjuvant compositions and the vaccine compositions of the present invention may be incorporated into drinking water or food and fed to an animal. The present invention includes drinking water and food comprising the vaccine adjuvant composition and the vaccine composition of the present invention.

The vaccine adjuvant composition and the vaccine composition of the present invention may be administered once or in several separate instances at intervals of two days to eight weeks.

Administration of the vaccine adjuvant composition of the present invention alone or in combination with a vaccine to an animal results in an increase in Th1 cells, a reduction of production of allergy-specific IgE antibody, and an increase in the production of IgG2 antibody or IgG2a antibody acting as a protective antibody against infectious diseases. As a result, allergic symptoms can be suppressed in animals, and allergic diseases can be treated. In addition, infections can be prevented or treated.

The present invention is described in greater detail with reference to the following examples, although the present invention is not limited to these examples.

[Comparative Example] Synthesis of Hemin Chloride by Conventional Method (Usual Method)

Hemin chloride was obtained from Sigma (Catalog Number: 51280; purity determined via HPLC: ≥98%).

Hemin chloride (45 mg) was dissolved in 4.5 ml of an NaOH solution, and 0.45 ml of 1 N hydrochloric acid was added thereto. Acetic acid was then added thereto with agitation at 60° C., so as to adjust the pH level to 4.8. The mixture was allowed to stand at room temperature overnight. Thus, β-hematin crystals were formed. Subsequently, a precipitate was obtained via centrifugation, the precipitate was washed by centrifugation three times with the use of a 0.1 M sodium bicarbonate buffer containing 2% SDS (pH 9.1), and the resultant was further washed by centrifugation 6 to 8 times with purified water for replacement with purified water.

FIG. 4 shows the procedure of the Usual method. According to the Usual method, as shown in FIG. 4, the supernatant (referred to as "Usual-sup") and the precipitate (referred to as "Usual-pellet") were obtained upon centrifugation by washing with purified water, the precipitate was sterilized using an autoclave (121° C., 20 minutes), and properties of the resultant (referred to as "Usual-AC") were then examined.

[Example 1] Synthesis of β-Hematin by the Heat Method of the Present Invention

Hemin chloride was obtained from Tokyo Chemical Industry Co., Ltd. (TCI) (Catalog Number: H 0008; purity determined via the chelate method: ≥95%). Hemin chloride obtained from Sigma (purity determined via HPLC: >98%) was also used in order to verify that β-hematin equivalent to that obtained with the use of hemin chloride obtained from TCI could be produced. Hereafter, the experiment with the use of hemin chloride obtained from TCI is described.

Hemin chloride (100 mg) was dissolved in 10 ml of a 1 N NaOH solution, and 1 ml of a 1 N HCl aqueous solution was added thereto. In addition, acetic acid was added dropwise thereto, so as to adjust the pH level to 4.5 to 4.8. Subsequently, a mixture containing hemin chloride was heated to 80° C. or higher for 1 to 3 hours. Heating was carried out in a water bath. Following the heating, washing by centrifugation was carried out once with the use of an aqueous solution of disodium phosphate (pH 9.0), and the resultant was washed by centrifugation with purified water 3 or 4 times for replacement. Thus, β-hematin was obtained in a crystalline form. The resulting β-hematin is referred to as "Heat-TCI." It may be sterilized using an autoclave (121° C., 20 minutes).

FIG. 3 shows the procedure of the Heat method.

[Example 2] Comparison of the Heat Method of the Present Invention with the Conventional Usual Method Concerning synthesis of β-hematin by the Heat method of the present invention and by the conventional Usual method, response rates for starting materials, recovery rates via centrifugation, and rates of remaining hemin chloride used as a starting material were determined in the manner described below.
Response Rates for Starting Materials:
β-Hematin was separated from hemin chloride in a sample via thin-layer chromatography and compared with the hemin chloride, which was separately spotted.
Recovery Rates Via Centrifugation:
The precipitate was dissolved using the 2% SDS+0.1M-NaOH, and the resultant was quantified by the absorption method using hemin chloride as a standard product.
Rates of Remaining Hemin Chloride:
β-Hematin was separated from hemin chloride via thin-layer chromatography and compared with the hemin chloride, which was separately spotted.

In addition, the color of the β-hematin suspension obtained by the Heat method and that of the β-hematin suspension obtained by the Usual method were visually inspected, the primary particle configuration and size (the maximal size) of the synthesized β-hematin crystal were determined via SEM, and the particle size distribution was determined using a laser diffraction/scattering particle size distribution measuring apparatus. A slide glass was coated with poly-L-lysine, it was allowed to adsorb β-hematin, and an image was obtained with the use of an ultra-high resolution FESEM (field emission-type scanning electron microscope; S-4800, Hitachi, Ltd.) to determine particle sizes. The particle size distribution in the β-hematin suspension was determined using a wet laser diffraction/scattering particle size distribution measuring apparatus (LA-950V2, Horiba, Ltd.).

FIG. 5 shows response rates for starting materials, recovery rates via centrifugation, rates of remaining hemin chloride, color of β-hematin obtained, maximal primary particle size of β-hematin, and particle size distribution attained by the Heat method and by the Usual method.

While the response rates for starting materials were 50% to 60% in accordance with the conventional Usual method, the response rates were higher than 95% in accordance with the Heat method of the present invention. While the recovery rates via centrifugation of Usual (pellet) and Usual-sup obtained by the Usual method were 10% to 30% and 10% to 20%, respectively, those obtained by the Heat method of the present invention were 90% to 98%. While the rates of remaining hemin chloride in Usual (pellet), Usual-sup, and Usual-AC obtained by the Usual method were 20% to 30%, about 10%, and about 10%, respectively, in addition, those obtained by the Heat method of the present invention were less than 2%.

As is apparent from the results demonstrated above, β-hematin could be synthesized with a high yield, and the purity thereof was high, in accordance with the Heat method.

While the maximal primary particle size of Usual (pellet) obtained by the Usual method was 0.2 to 0.8 μm, that of Usual-sup was 0.1 to 0.5 μm, and that of Usual-AC was 0.3 to 2 μm, the maximal primary particle size of the β-hematin obtained by the Heat method of the present invention was somewhat greater, which was 0.5 to 5 μm. While the particle size distribution range of Usual (pellet) obtained by the Usual method was 1 to 50 μm, that of Usual-sup was 0.05 to 2 μm, and that of Usual-AC was 0.1 to 1 μm, the particle size distribution range of β-hematin obtained by the Heat method of the present invention was 0.2 to 5 μm. The median size (average particle size) of Usual (pellet) obtained by the Usual method was 5 to 15 μm, that of Usual-sup was 0.1 to 0.6 μm, and that of Usual-AC was 0.1 to 0.5 μm. In contrast, the particle size distribution range of β-hematin obtained by the Heat method of the present invention was 0.6 to 1.2 μm. The dispersion state of β-hematin obtained by the Heat method was superior to that of β-hematin obtained by the Usual method, it was stabilized with uniform particle size distribution, and aggregation was less likely to occur.

Figure 7:
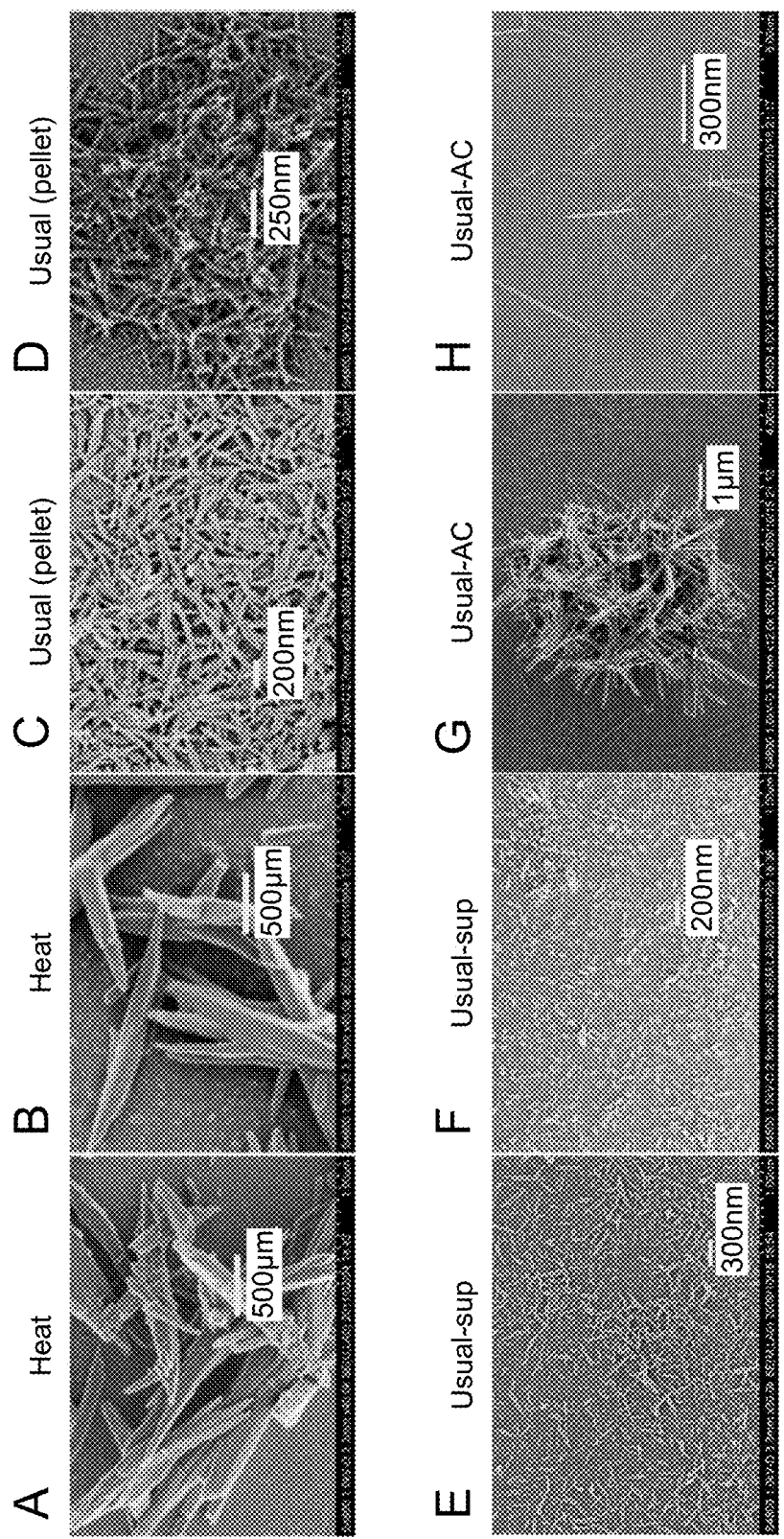
FIG. 7 shows scanning electron microscopic images of β-hematin synthesized by the Heat method and the Usual method.

FIG. 6 shows microscopic images of β-hematin obtained by the Heat method and β-hematin obtained by the Usual method; i.e., Usual (pellet), Usual-sup, and Usual-AC, (magnification: 200×). In FIG. 6, A and B each show the β-hematin produced by the Usual method, and E and F each show the β-hematin produced by the Heat method. In FIG. 6, also, C shows Usual-AC, and D shows Usual-sup. FIG. 7 shows scanning electron microscopic images of crystals. In FIG. 7, A and B each show the β-hematin produced by the Heat method, and C and D each show the β-hematin produced by the Usual method. In FIG. 7, also, E and F each show Usual-sup, and G and H each show Usual-AC. In FIG. 7, the scale bar represents the size. The scale bars in FIGS.

7A and 7B are each 500 μm, the scale bar in FIG. 7C is 200 nm, the scale bar in FIG. 7D is 250 nm, the scale bar in FIG. 7E is 300 nm, the scale bar in FIG. 7F is 200 nm, the scale bar in FIG. 7G is 1 μm, and the scale bar in FIG. 7H is 300 nm.

Figure 8:
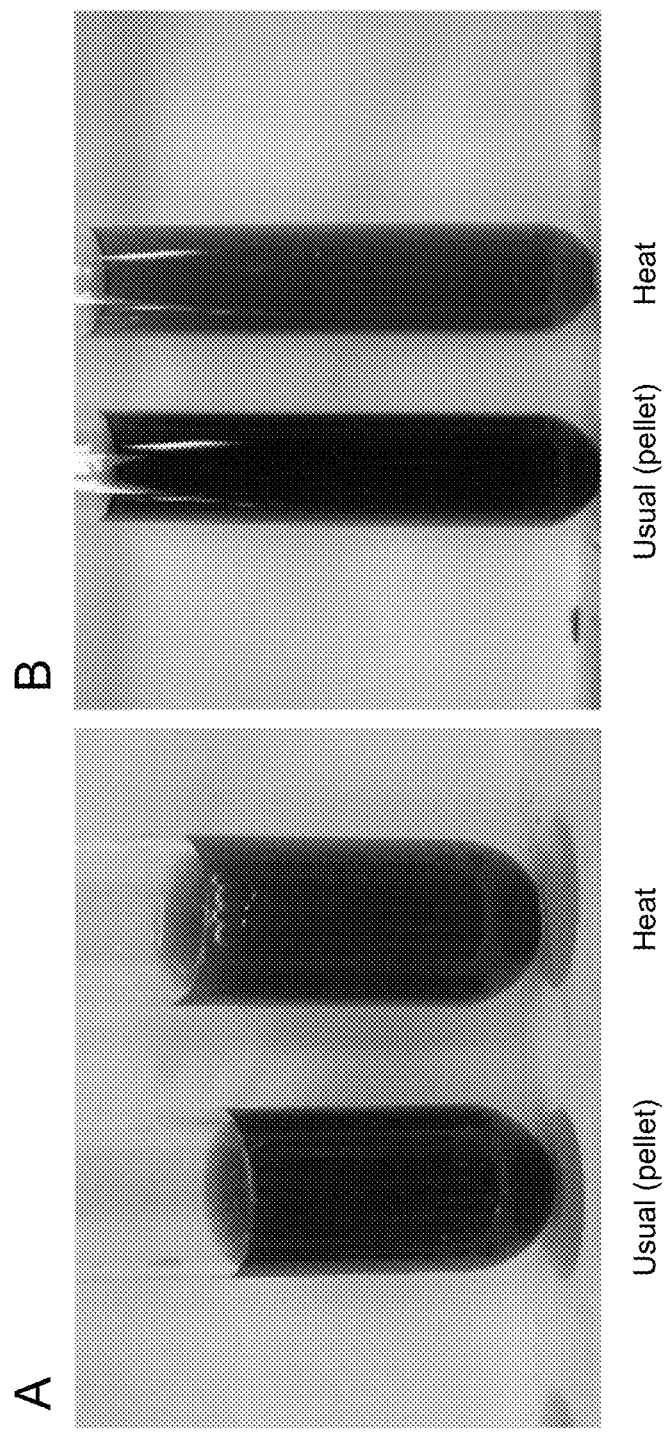
FIG. 8 shows a difference in color of β-hematin synthesized by the Heat method from that synthesized by the Usual method.

FIG. 8 shows a difference between the color of a suspension of the β-hematin produced by the Heat method and the color of a suspension of the β-hematin produced by the Usual method. FIG. 8A and FIG. 8B show the colors of suspensions of β-hematin with different particle densities. Specifically, the color of the suspension produced by the Heat method was grayish-brown to black. In contrast, the color of the suspension produced by the Usual method was reddish-brown to black. Such difference in color is considered to result from the structural difference between the β-hematin produced by the Heat method and the β-hematin produced by the Usual method; that is, the difference in the state of coordination to iron atoms and the difference in crystallinity.

[Example 3] Property Analysis of the β-Hematin Produced by the Heat Method of the Present Invention (Usual (Pellet)) Via Infrared Spectrometry (IR), Powder X-Ray Diffractometry, Solid-State Nuclear Magnetic Resonance ($^1$H-NMR) Spectroscopy, Raman Spectrometry, Electron Spin Resonance (ESR) Analysis, Structural Analysis Via Near-Infrared Spectrometry (NIR) and Ultraviolet-Visible Spectroscopy (UV-Vis), and Thermogravimetric/Differential Thermal Analysis (TG-DTA)

Structural Analysis Via Infrared Spectrometry

Figure 9:
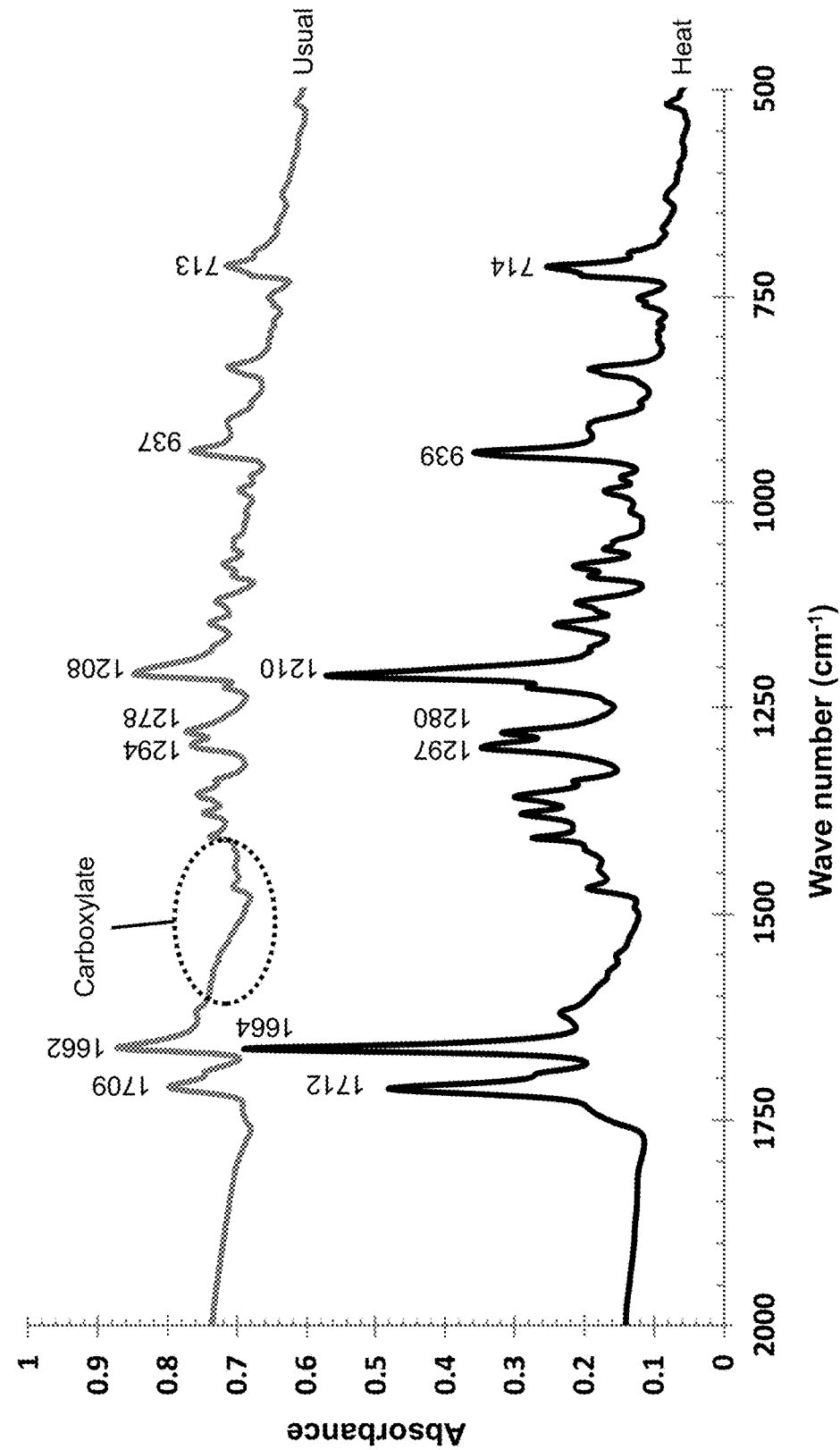
FIG. 9 shows a difference in spectra of β-hematin synthesized by the Heat method and the Usual method determined via infrared spectroscopy by the potassium bromide tablet method (KBr tablet method).
Figure 10:
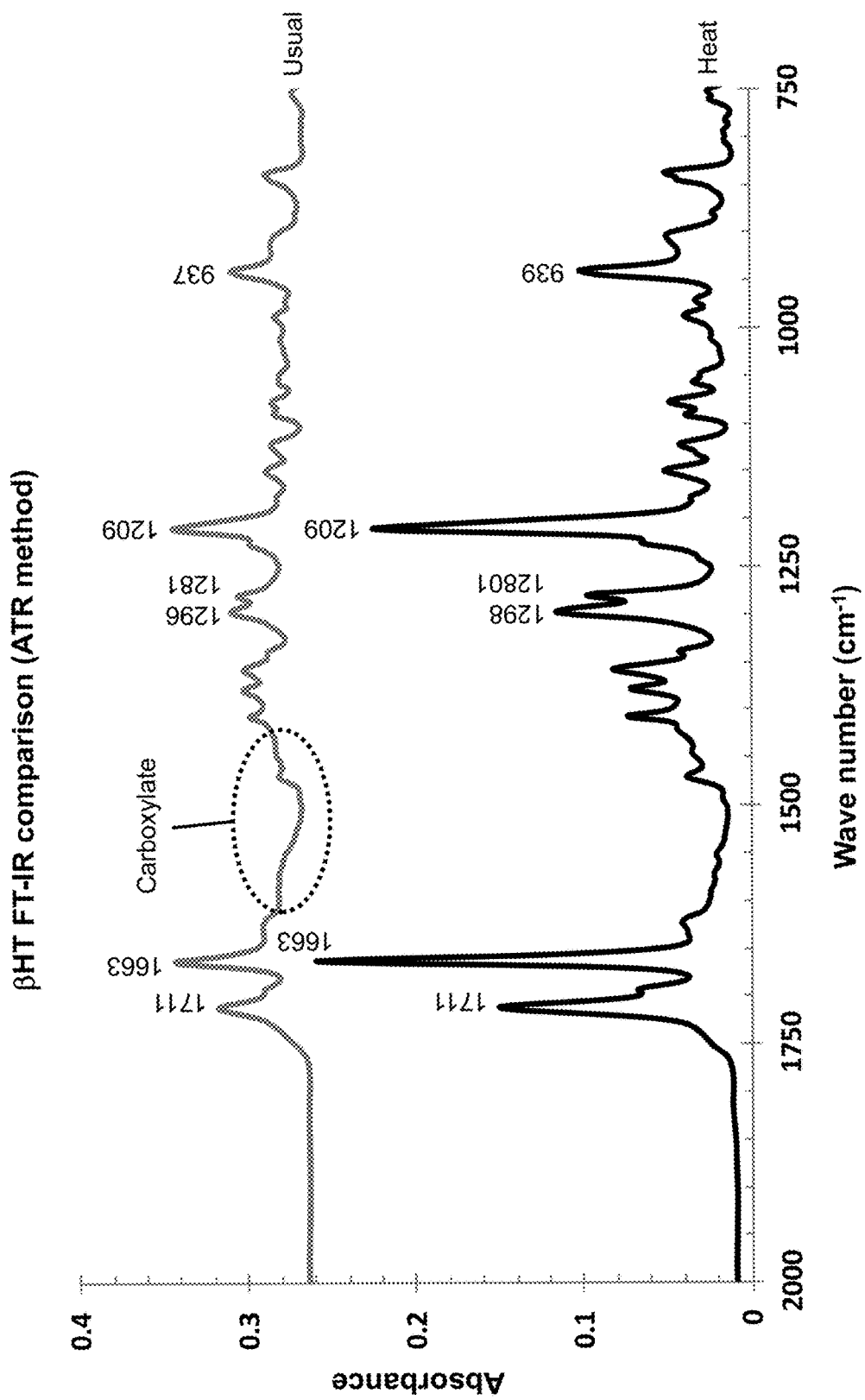
FIG. 10 shows a difference in spectra of β-hematin synthesized by the Heat method and the Usual method determined via ATR infrared spectroscopy.

The dehydrated sample was mixed with potassium bromide, the mixture was subjected to compression molding, and the resulting pellets were subjected to transmission spectrometry via Fourier transform infrared spectroscopy (KBr tablet method). In a powder state, also, the spectrum was determined by the ATR method (attenuated total reflectance) with a Ge-prism at a 45° angle of incidence. Measurement was carried out under a nitrogen atmosphere using Varian-7000 (manufactured by Varian; special ceramic light source; deuterated triglycine sulfate (DTGS) detector). The results are shown in FIG. 9 (KBr tablet method) and in FIG. 10 (ATR method).

The β-hematin produced by the Heat method and the β-hematin produced by the Usual method exhibited characteristic main peaks at around 1710 cm$^{-1}$, 1662 cm$^{-1}$, 1297 cm$^{-1}$, 1280 cm$^{-1}$, 1209 cm$^{-1}$, 939 cm$^{-1}$, and 714 cm$^{-1}$, and the primary structures thereof were substantially equivalent to each other. However, the peak width of the main absorption band of the β-hematin produced by the Heat method was observed to be sharper. That is, such β-hematin was considered to have higher crystallinity resulting from higher crystal density and higher single crystal proportion. In the case of the β-hematin produced by the Usual method, peaks were detected in a broad range at around 1600 cm$^{-1}$ to 1500 cm$^{-1}$ and 1420 cm$^{-1}$ to 1350 cm$^{-1}$, and large quantities of carboxylic acids or carboxylates other than Fe—COO bonds were present. The baseline of the spectrum for the β-hematin produced by the Usual method sloped down to the right because of the color of the sample. In comparison with the β-hematin produced by the Heat method, main peak shifts of approximately 2 cm$^{-1}$ were observed in the lower frequency region. That is, a poor state of dispersion and spectral asymmetry were observed.

Crystalline Structure Analysis Via Powder X-Ray Diffractometry

Figure 11:
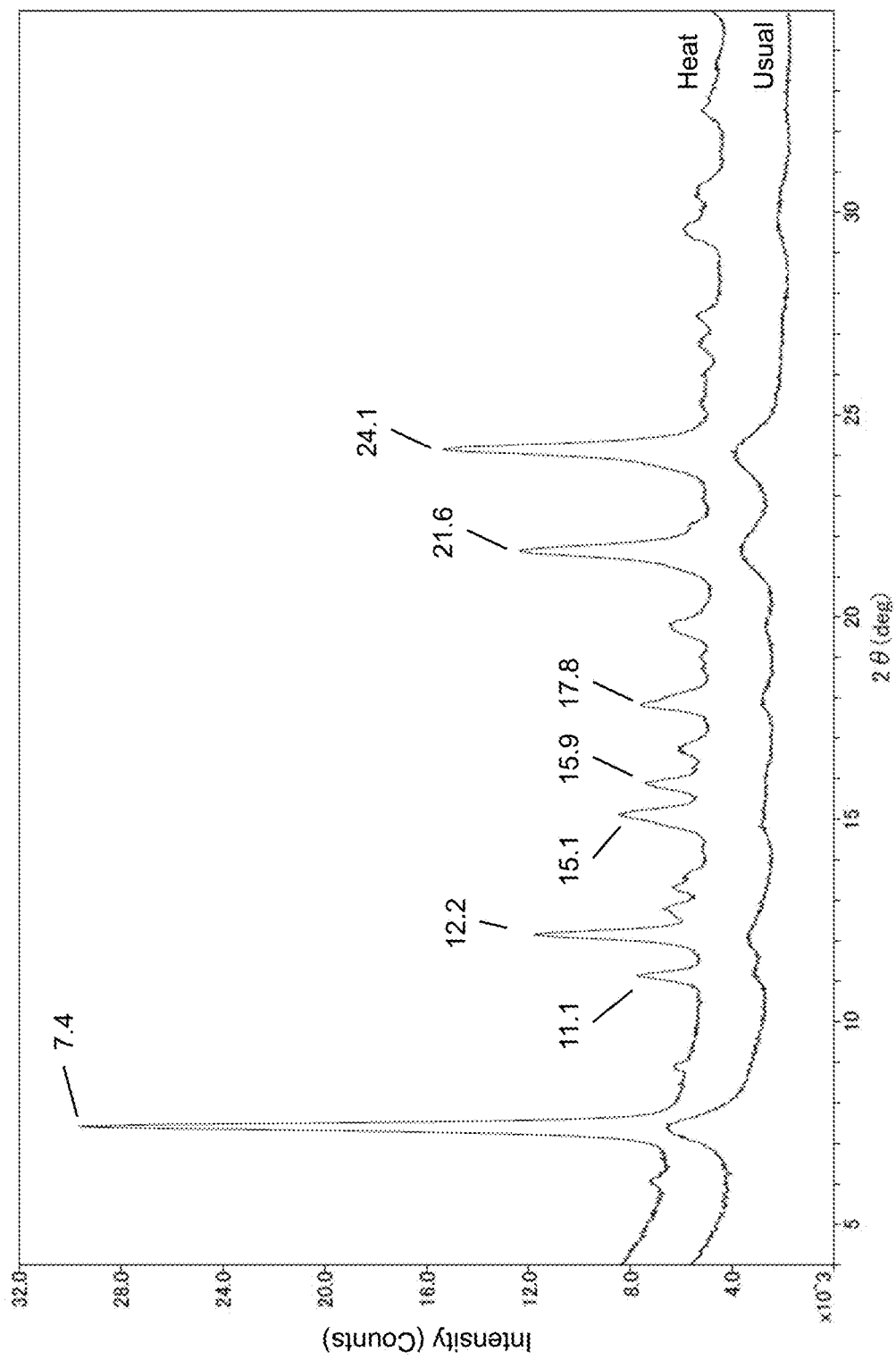
FIG. 11 shows a difference in spectra of β-hematin synthesized by the Heat method and the Usual method determined via powder X-ray diffractometry.

The dehydrated sample was mounted on a non-reflective silicone plate and subjected to wide-angle X-ray diffractometry. Measurement was carried out using D8 ADVANCE (sealed tube type, manufactured by Bruker AXS, using Cu—K ray (Ni filter) as an X-ray source, LynxEye detector) at the output of 40 kV/40 mA with a slit system of Div. Slit: 03°. The results are shown in FIG. 11.

The β-hematin crystal produced by the Heat method exhibited main peaks characteristics for angles of diffraction (2θ) at around 7.4°, 12.2°, 21.6°, and 24.1°, the β-hematin crystal produced by the Usual method exhibited the similar peaks, and two strong 2θ peaks were consistent with the values concerning hemozoin disclosed in the literature. However, the peak intensity of the β-hematin crystal produced by the Heat method was higher, and the band width thereof was sharper. The crystallite size of the β-hematin synthesized by the Heat method was greater than that of the β-hematin synthesized by the Usual method, and the degree of crystallinity thereof was higher, although crystal forms were substantially the same.

Structural Analysis Via Solid-State NMR Spectroscopy

Figure 12:
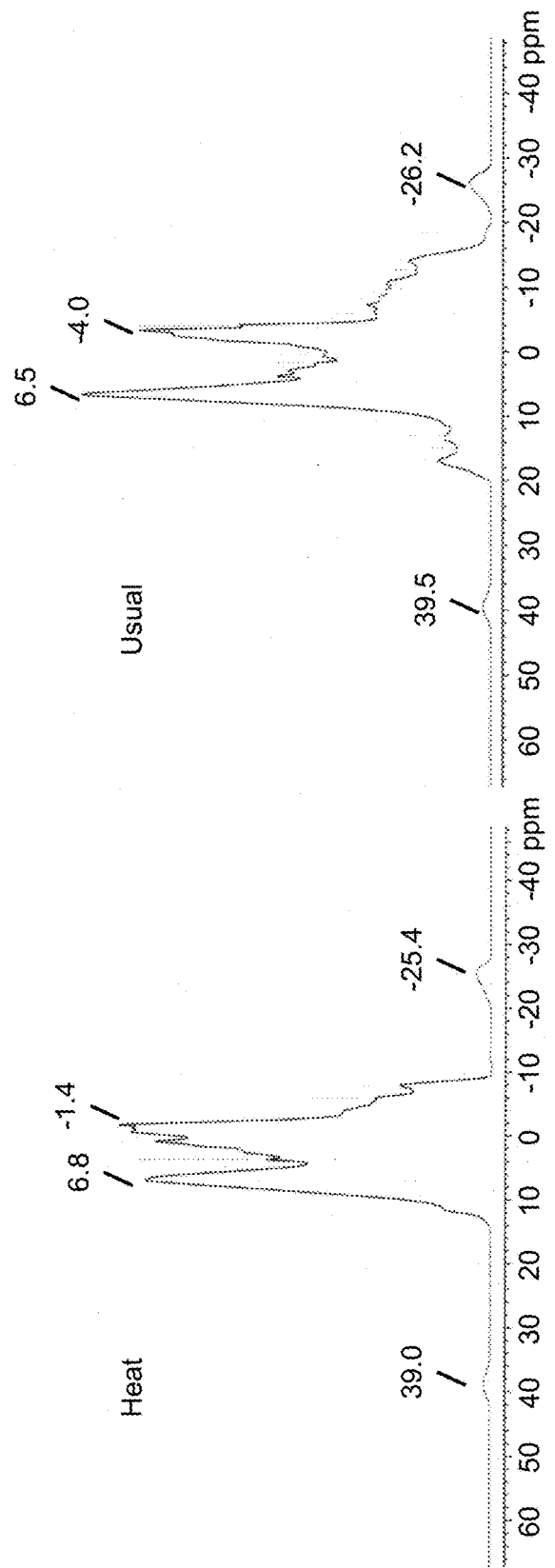
FIG. 12 shows a difference in spectra of β-hematin synthesized by the Heat method and the Usual method determined via solid-state H-NMR spectroscopy.

The dehydrated samples were introduced into cells (3.2φ; number of rotations: 20K) and subjected to high-speed solid-state $^1$H-NMR spectroscopy using the Varian NMRJ 600 MHz spectrometer. The results are shown in FIG. 12.

The β-hematin crystal produced by the Heat method exhibited main peaks at 6.8 ppm and −1.4 ppm, and the β-hematin crystal produced by the Usual method exhibited main peaks at 6.5 ppm and −4.0 ppm. Because of the magnetic properties of iron, a spectrum with a high degree of separation could not be obtained, and identification was difficult; however, spectral configurations thereof were different from each other.

Because substantially no structural difference was observed via IR, it was considered that there was a structural difference in, for example, hexacoordination of a hydroxyl group to an iron atom.

Structural Analysis Via Raman Spectrometry

Figure 13:
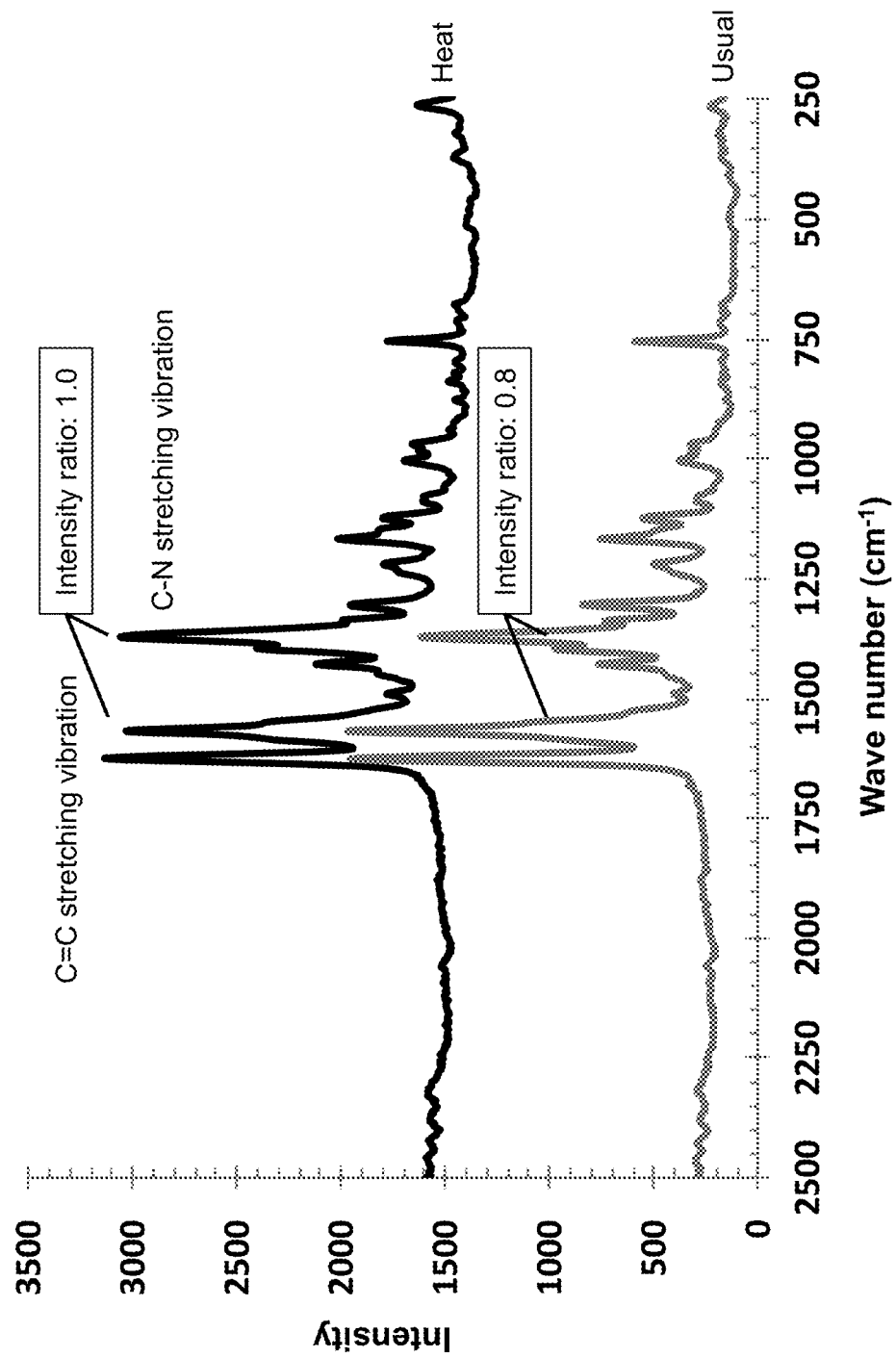
FIG. 13 shows a difference in spectra of β-hematin synthesized by the Heat method and the Usual method determined via Raman spectrometry at an excitation wavelength of 514.4 nm.
Figure 14:
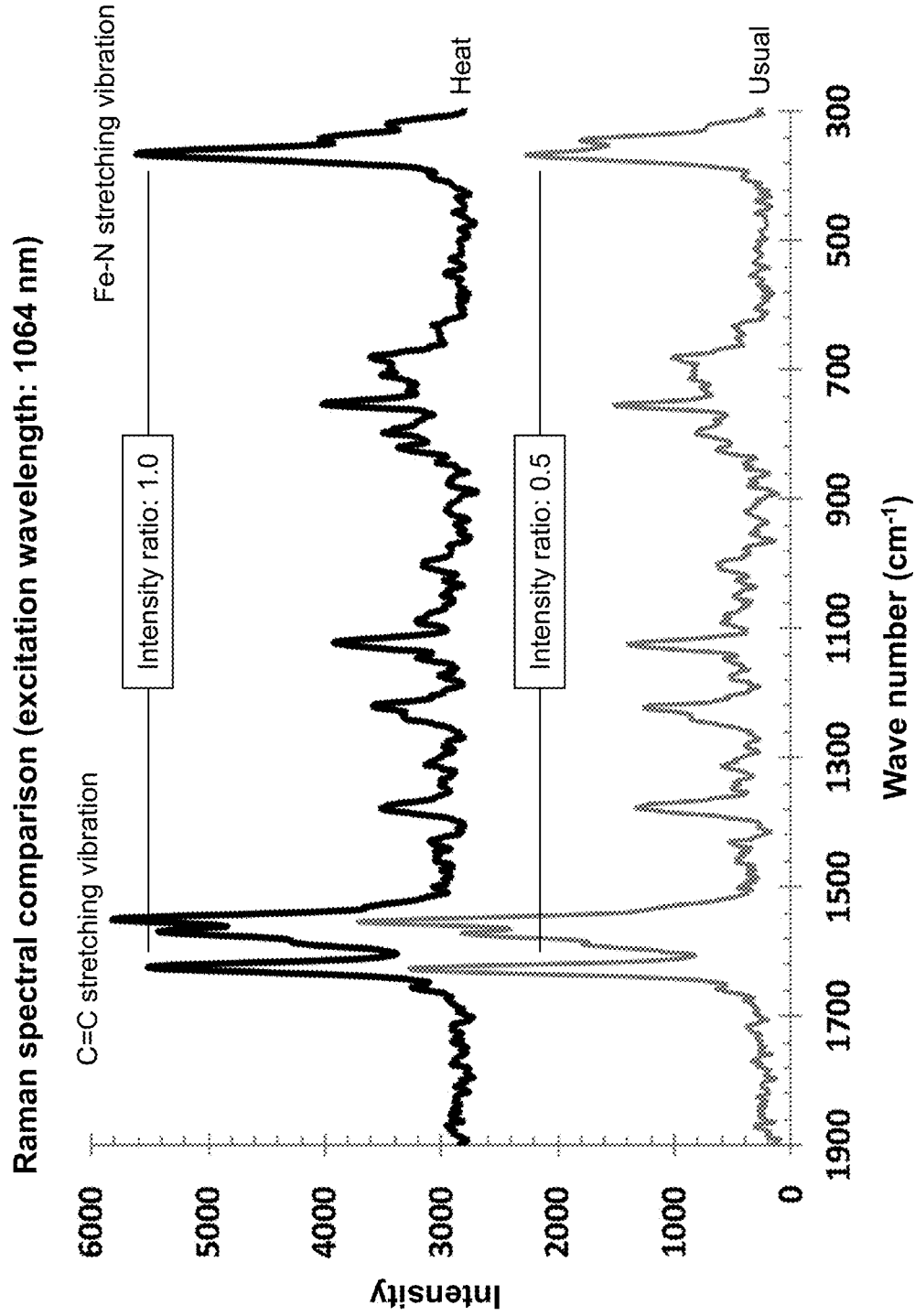
FIG. 14 shows a difference in spectra of β-hematin synthesized by the Heat method and the Usual method determined via Raman spectrometry at an excitation wavelength of 1064 nm.

The dehydrated samples were subjected to laser Raman spectrometry using PDP-320 (manufactured by Photon Design Corporation) at excitation wavelengths of 514.4 nm (light source: Ar+; beam diameter: 1 μm; laser power: 8 to 12 mW/NDF·35 mW/20%+NDF; CCD detector) and 1064 nm (light source: YAG; beam diameter: 1 μm; laser power: 200 mW/80°; InGaAs detector). The results are shown in FIG. 13 (514.4 nm) and in FIG. 14 (1064 nm).

As a result of Raman spectrometry conducted at excitation wavelengths of 514.4 nm (FIG. 13) and 1064 nm (FIG. 14), the β-hematin crystal produced by the Heat method and the β-hematin crystal produced by the Usual method were found to exhibit substantially the same peaks. Concerning peak intensities, there were differences in the intensity ratios of peaks between the β-hematin produced by the Heat method and the β-hematin produced by the Usual method. Such phenomena were considered to result from changes in the electronic state caused by different inter-molecular interactions, different states of coordination to iron atoms, or different crystallinity.

Analysis of Spin State Via ESR

Figure 15:
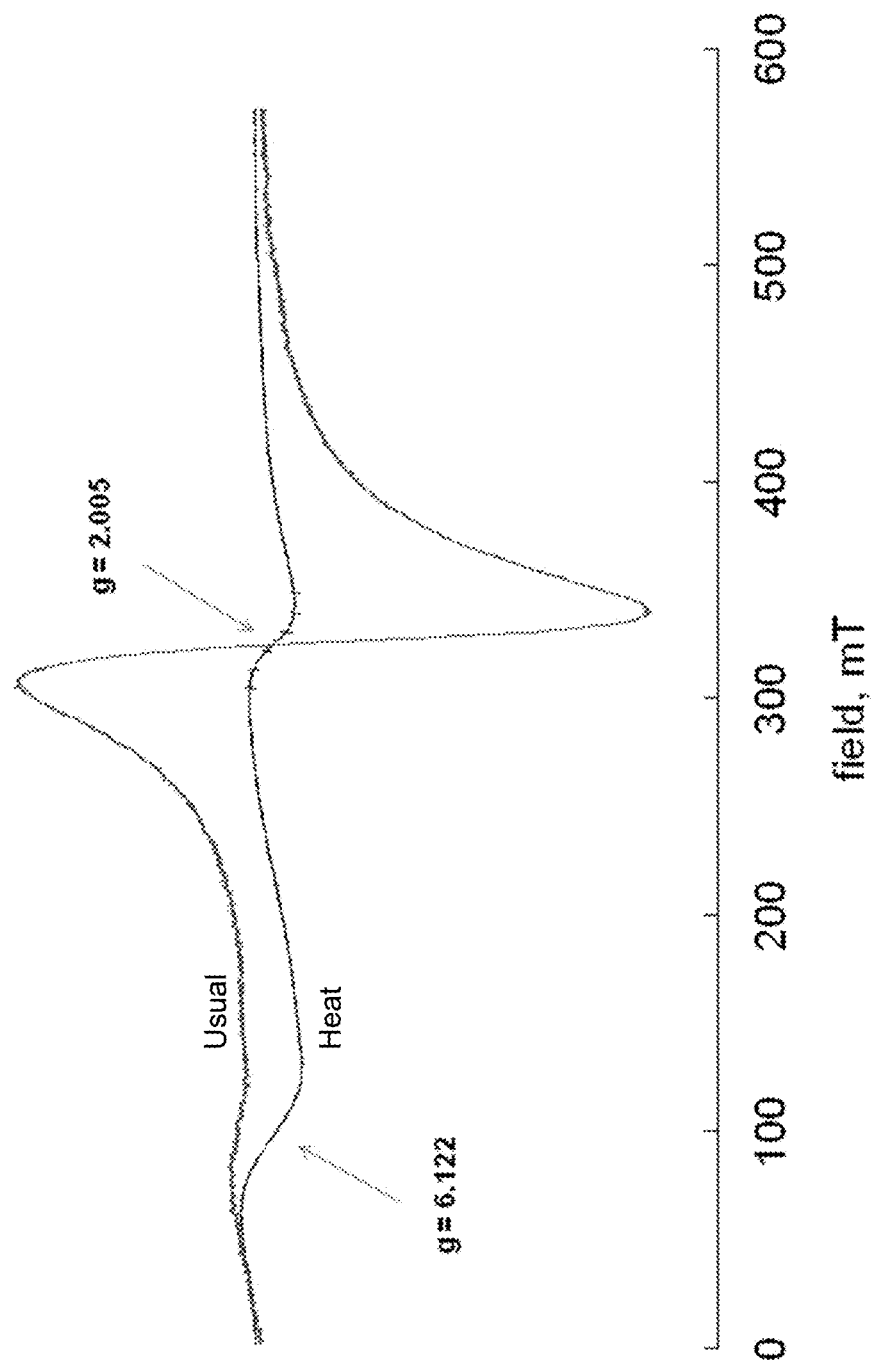
FIG. 15 shows a difference in spectra of β-hematin synthesized by the Heat method and the Usual method determined via ESR spectrometry at room temperature.
Figure 16:
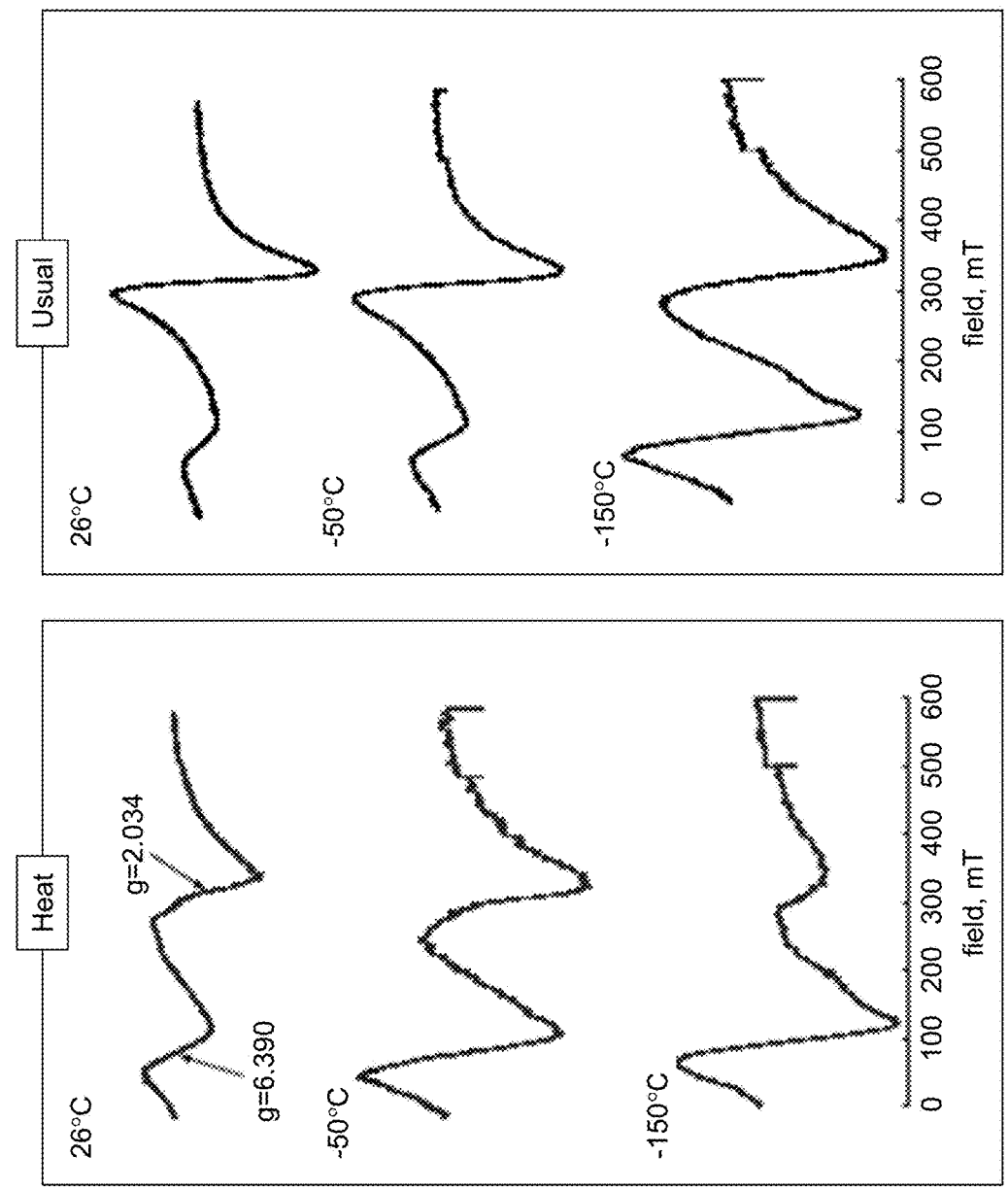
FIG. 16 shows a difference in spectra of β-hematin synthesized by the Heat method and the Usual method determined via ESR spectrometry at −50° C. and −150° C.

The dehydrated samples were introduced into cylindrical quartz cells (outer diameter: 5 mm) and subjected to ESR spectrometry using the JES RE-2X ESR spectrometer (manufactured by JEOL Ltd.) at room temperature, −50° C., and −150° C. The results of spectrometry conducted at room temperature are shown in FIG. 15, and the results of spectrometry conducted at room temperature, −50° C., and −150° C. are shown side by side in FIG. 16.

The β-hematin crystal produced by the Heat method exhibited two apparent signals at around 0 to 200 mT (g=6.122) and around 200 to 400 mT (g=2.005). The β-hematin produced by the Usual method exhibited substantially no signals at around 0 to 200 mT in the lower magnetic field. Also, there were differences in the signal intensity absolute values, and the β-hematin produced by the Usual method exhibited an integral of signals appearing in a broad range at around 200 to 400 mT, which was approximately 13 times greater than that exhibited by the β-hematin produced by the Heat method. When measurement was carried out at −50° C., the β-hematin produced by the Usual method exhibited a slight change in the lower magnetic field (around 0 to 100 mT), and the β-hematin produced by the Heat method exhibited a significantly elevated signal in the higher magnetic field (around 200 to 300 mT). That is, the signal at around 0 to 100 mT detected via ESR spectrometry conducted at −50° C. was stronger than the signal at around 200 to 300 mT, and such difference became more apparent at −150° C. The β-hematin produced by the Usual method exhibited no change in the higher magnetic field (around 200 to 300 mT) and elevation in the lower magnetic field (around 0 to 100 mT). In contrast, the β-hematin produced by the Heat method exhibited elevation in the lower magnetic field (around 0 to 100 mT) and a lowered signal in the higher magnetic field (around 200 to 300 mT). That is, the signal detected at around 0 to 100 mT was found to be at least twice the signal detected at around 200 to 300 mT as a result of ESR analysis at −150° C. The results demonstrate that there are significant differences in paramagnetic species types and densities. While the β-hematin produced by the Usual method exhibited a low-spin state for trivalent iron, the β-hematin produced by the Heat method exhibited a lower signal intensity than the β-hematin produced by the Usual method. In addition, the β-hematin produced by the Heat method exhibited complicated spectra involving a low-spin state and a high-spin state. Such phenomena are considered to result from different states of coordination to iron atoms and different Fe(III)-Fe(III) interactions.

Analysis Via Near-Infrared Spectrometry (NIR)

Figure 17:
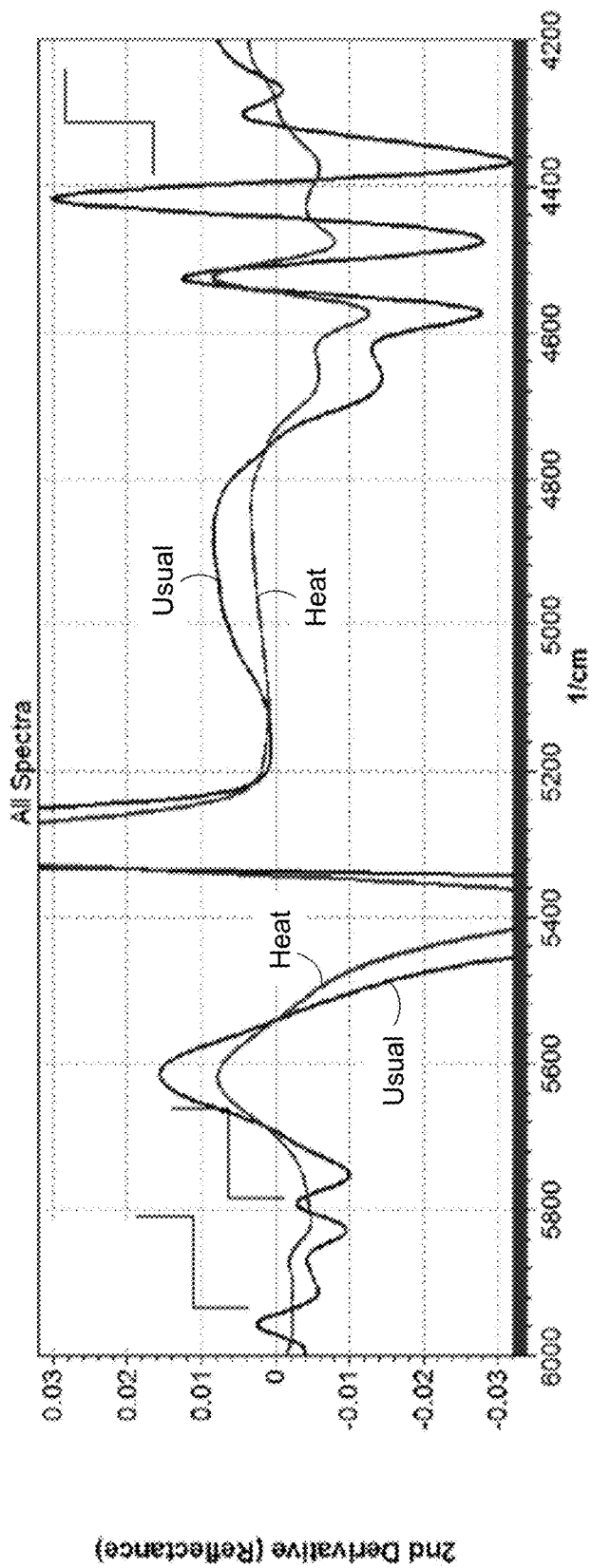
FIG. 17 shows a difference in spectra of β-hematin synthesized by the Heat method and the Usual method determined via near-infrared spectroscopy.

The samples were subjected to near-infrared spectrometry using the Fourier transform near-infrared spectrometer (NIRFlex N-500, manufactured by BUCHI Corporation). The results are shown in FIG. 17.

The near-infrared spectrum of the β-hematin crystal produced by the Heat method exhibited a lower reflectance throughout the wavenumber region than the spectrum of the β-hematin produced by the Usual method. While peaks were detected at 4440 cm$^{-1}$, 5780 cm$^{-1}$, and 5960 cm$^{-1}$ in the case of the β-hematin produced by the Usual method, substantially no peaks were observed in the β-hematin produced by the Heat method. This is considered to result from changes in OH and CH. In addition, differences in the spectral configuration as a whole lead to differences in configuration, such as crystalline structure and particle size.

Analysis Using Ultraviolet-Visible Spectrometer (UV-Vis)

Figure 18:
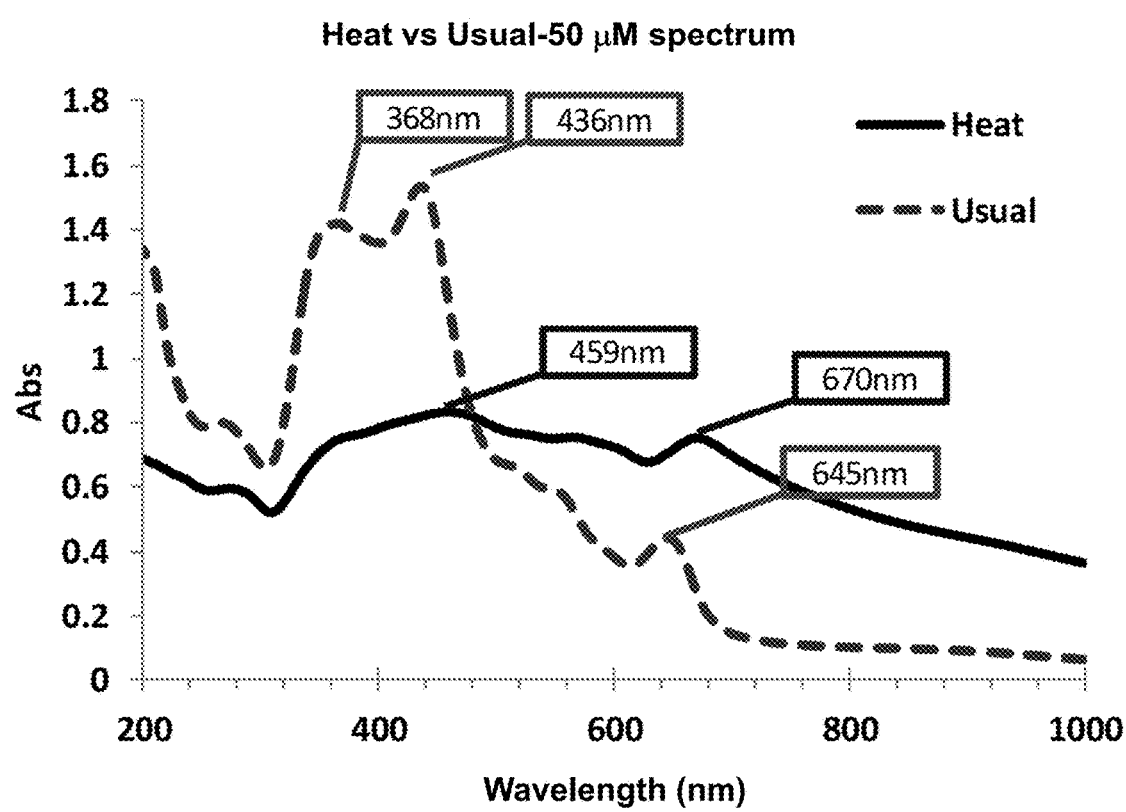
FIG. 18 shows a difference in spectra of β-hematin synthesized by the Heat method and the Usual method determined via ultraviolet-visible spectroscopy.

The samples were subjected to ultraviolet-visible spectrometry using the ultraviolet-visible spectrometer (V-630DS, manufactured by JASCO Corporation). The results are shown in FIG. 18.

The β-hematin crystal produced by the Heat method exhibited spectra with peaks at 493 nm and 670 nm and small differences in the absorbance from 200 nm to 1000 nm. The β-hematin crystal produced by the Usual method exhibited spectra with peaks at 368 nm, 436 nm, and 645 nm and strong absorption from 300 nm to 500 nm. The results demonstrate that the color of particles or suspensions differs from each other and there are structural differences.

Analysis Via Thermogravimetric/Differential Thermal Analysis (TG-DTA)

Figure 19:
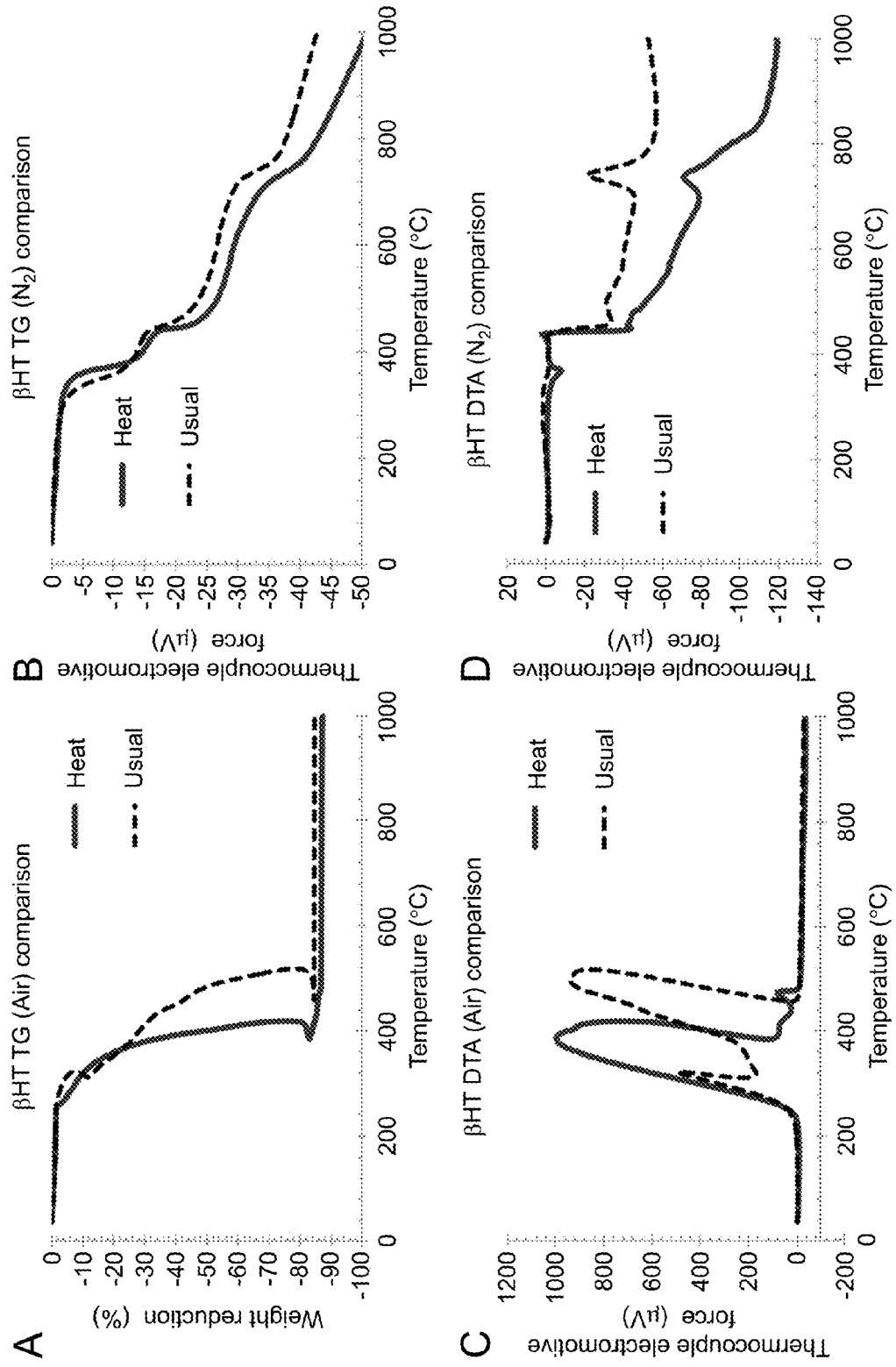
FIG. 19 shows changes in weight reduction and differential heat variation of β-hematin synthesized by the Heat method and the Usual method under heating determined via thermogravimetric/differential thermal analysis.

The dehydrated samples were subjected to thermogravimetric analysis and differential thermal analysis using Thermo plus EvoII TG-DTA (Rigaku Corporation). The results are shown in FIG. 19. In FIG. 19, A, B, C, and D each show the results of comparison of thermal mass spectrometry (TG) in the air (TG (Air)), the results of comparison of thermal mass spectrometry (TG) in nitrogen (TG ($N_2$)), the results of comparison of thermogravimetric DTA in the air (DTA (Air)), and the results of comparison of thermogravimetric DTA in nitrogen (DTA ($N_2$)).

As a result of thermogravimetric/differential thermal analysis in the air, the β-hematin crystal produced by the Heat method was found to undergo thermacogenesis at around 250° C. and rapid oxidative decomposition up to 400° C. In nitrogen, thermal decomposition involving endothermic changes took place at around 360° C. and around 440° C., and thermal decomposition involving thermacogenesis took place at around 700° C.

While the behavior of the β-hematin crystal produced by the Usual method was substantially the same as that of the β-hematin produced by the Heat method, two-phase oxidative decomposition continued up to around 500° C. in the air. In nitrogen, the first-phase thermal decomposition took place at around 300° C., which was earlier than the β-hematin produced by the Heat method, and the reduction in weight because of decomposition at the second and subsequent phases was slighter than that observed in the β-hematin produced by the Heat method. The results demonstrate that the proportion of impurities or particles with different crystalline forms (or amorphous particles) in the β-hematin produced by the Usual method is greater than that observed in the β-hematin produced by the Heat method.

In FIGS. 9 to 19, the term "Heat" indicates the results of analysis for the β-hematin produced by the Heat method, and the term "Usual" indicates the results of analysis for the β-hematin produced by the Usual method (Usual (pellet)).

Figure 20:
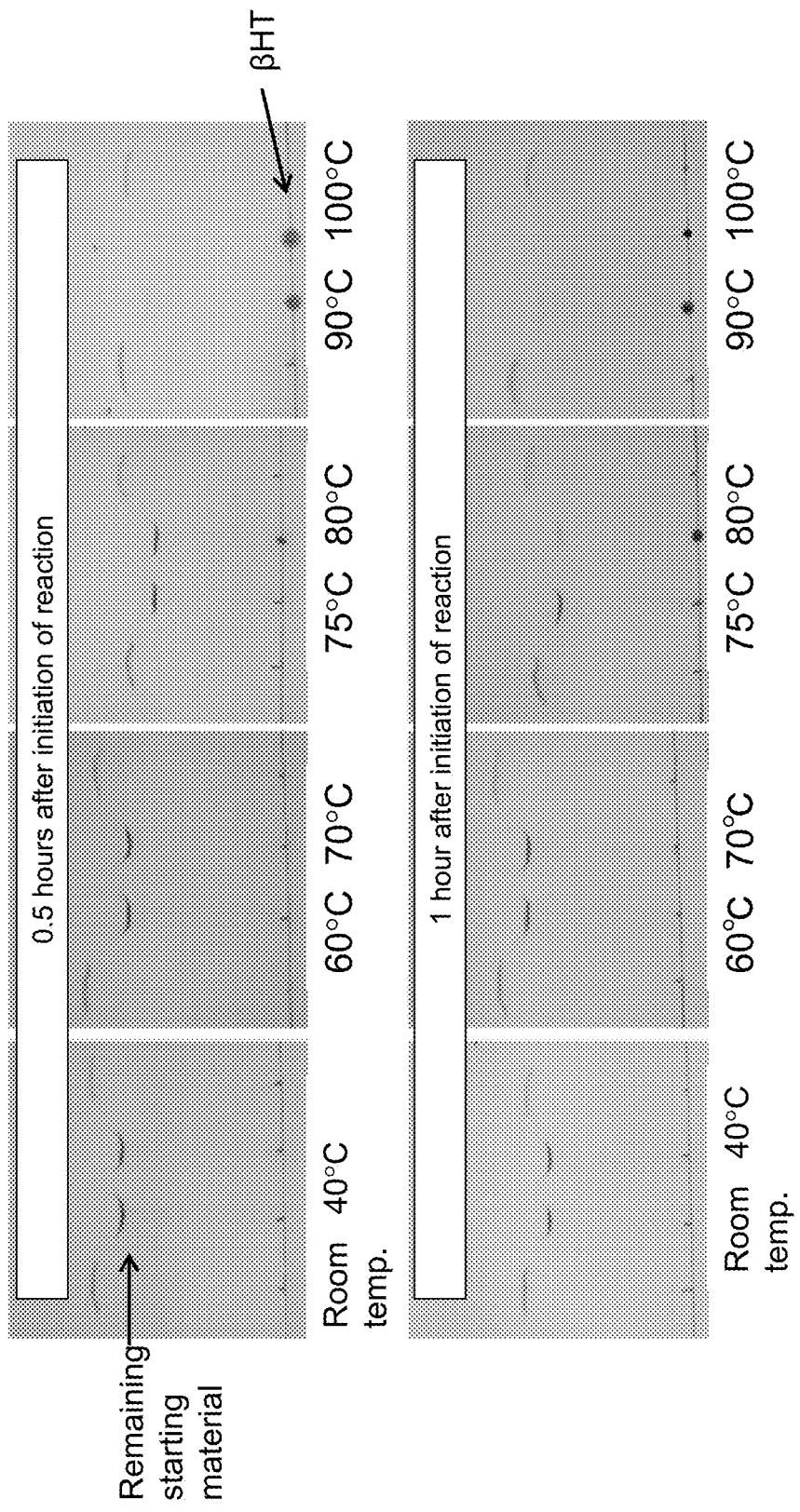
FIG. 20 shows a difference in reaction rates and the duration up to the completion of the reaction (i.e., the extent of reaction) at different reaction temperatures.

[Example 4] Inspection of Difference in Reaction Rate and Reaction Speed Caused by Different Synthesis Temperature in the Heat Method In the method of producing β-hematin by the Heat method, the reaction temperature was set to a level from room temperature to 100° C., and differences in the reaction rates (the decrease rates) for hemin chloride as a starting material and in the reaction speed were inspected. The results are shown in FIG. 20. Most starting materials disappeared within 30 minutes after the initiation of the reaction at 90° C. or higher and within 1 hour after the initiation of the reaction at 80° C. or higher. Since no spots were observed other than the starting material and β-hematin spots, almost all starting material was considered to be transformed into β-hematin at 80° C. or higher. The reaction did not substantially proceed at 75° C. or lower.

[Example 5] Test of Adjuvant Effects of β-Hematin Synthesized by the Heat Method of the Present Invention At least 3 mice were prepared. The β-hematin produced by the Heat method and the β-hematin produced by the Usual method (Usual (pellet) and Usual-sup) were diluted to 1 to 4 mM with PBS to prepare 200 μl of the sample solution, antigen ovalbumin (OVA) was added thereto, and the resultant was administered to the mice twice at intervals of 10 days. Blood samples were obtained 1 week and 3 weeks after the administration, and the amounts of anti-OVA IgG antibodies produced in the obtained sera were determined via ELISA.

Figure 21:
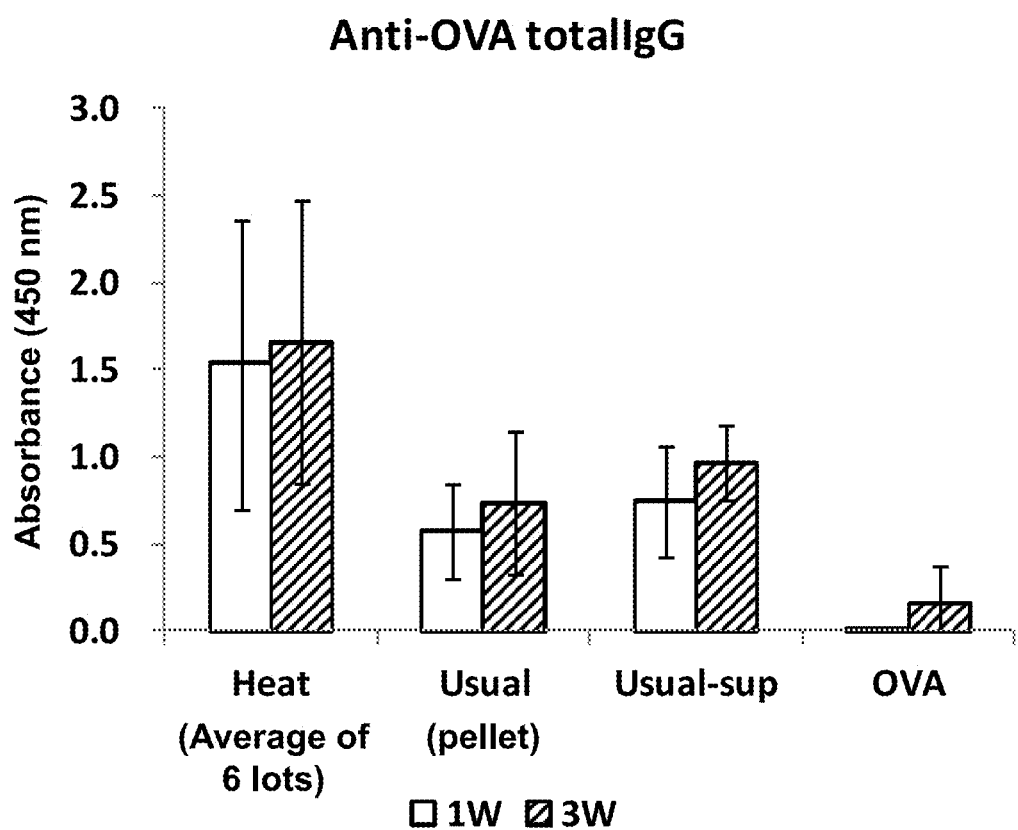
FIG. 21 shows a difference in adjuvant effects of β-hematin synthesized by the Heat method and the Usual method.

The results are shown in FIG. 21. As shown in the figure, an increase in the antibody titer obtained with the use of the β-hematin produced by the Heat method as an adjuvant was greater than that obtained with the use of the β-hematin produced by the Usual method as an adjuvant in the first week and in the third week. Such increase was particularly significant in the third week.

Figure 22:
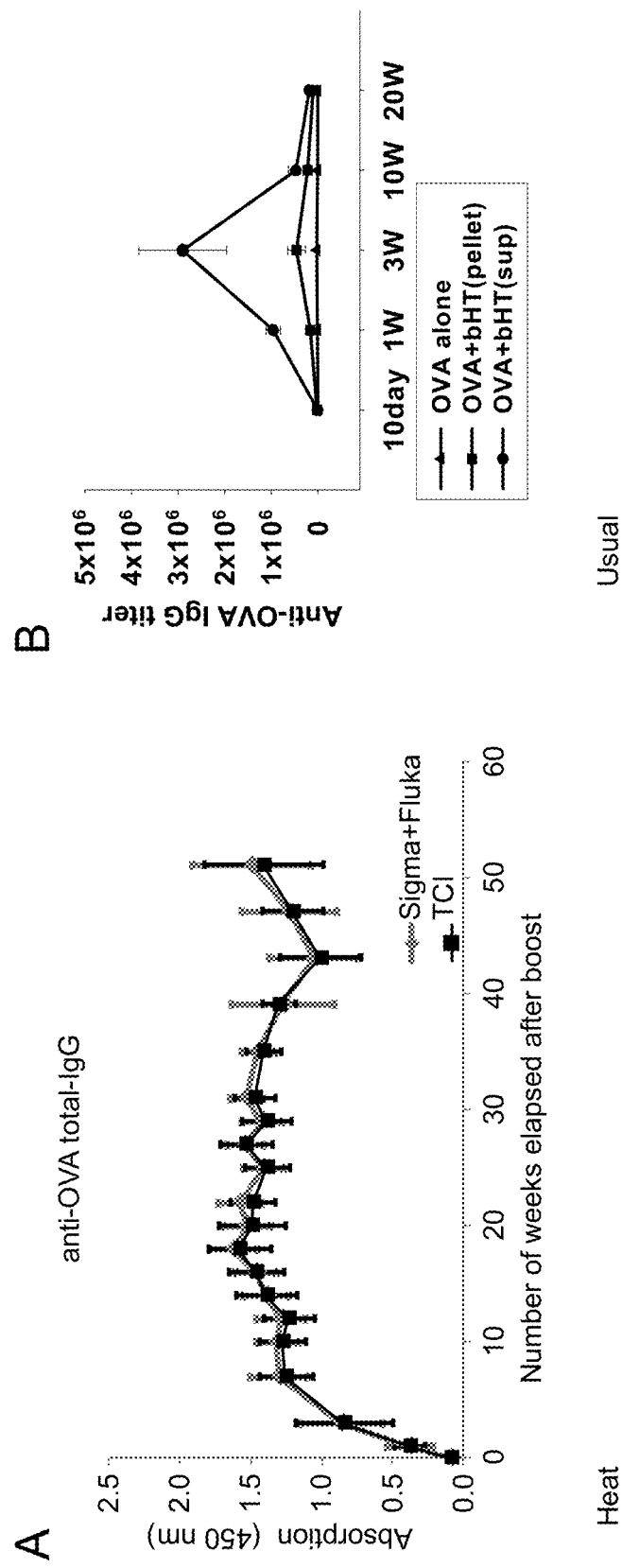
FIG. 22 shows a change in the capacity of β-hematin synthesized by the Heat method and the Usual method for prolonging antibody production.

Thereafter, measurement of the antibody titer in blood was continued up to the 50th week. The results are shown in FIG. 22. FIG. 22A shows the results attained with the use of the β-hematin produced by the Heat method, and FIG. 22B shows the results attained with the use of the β-hematin produced by the Usual method. FIG. 22A shows the results attained with the use of β-hematin produced using hemin chloride obtained from Tokyo Chemical Industry Co., Ltd. (TCI) as a starting material and the results attained with the use of β-hematin produced using hemin chloride obtained from Sigma as a starting material. FIG. 22B shows the results attained with the use of the supernatant (Usual-sup) and the precipitate (Usual (pellet)) obtained when producing β-hematin by the Usual method as adjuvants and the results attained with the administration of OVA alone without the use of β-hematin. As shown in FIG. 22, an increase in the antibody titer was observed in Usual-sup when the β-hematin produced by the Usual method was used, the antibody titer reached its peak 3 weeks after the administration, and it decreased thereafter. When the β-hematin produced by the Heat method was used, in contrast, a high antibody titer was maintained up to at least 50 weeks after the administration.

The results demonstrate that a high antibody titer can be maintained with the use of the β-hematin produced by the Heat method of the present invention as an adjuvant.

INDUSTRIAL APPLICABILITY

The β-hematin crystal and the vaccine adjuvant composition containing such β-hematin crystal according to the present invention can be used for prevention and treatment of allergic diseases and infectious diseases of animals, including humans, in the fields of medicine and veterinary medicine.

All publications, patents, and patent applications cited herein are incorporated herein by reference in their entirety.

The invention claimed is:

1. A method for producing β-hematin comprising adding an HCl aqueous solution to a solution of hemin chloride dissolved in an NaOH aqueous solution, adding acetic acid dropwise thereto so as to adjust the pH level to 4 to 6, and heating the resulting mixture to 80° C. or higher, wherein the β-hematin crystals have a needle-like morphology, an average particle size of 0.6 to 1.2 μm, and exhibit main peaks characteristics for angles of diffraction (2θ) of 7.4°, 12.2°, 21.6°, and 24.1° in an X-ray diffraction pattern obtained by powder X-ray diffractometry with Cu-Kα rays, wherein each peak includes a plus-minus 0.2° diffraction angle.

2. The method according to claim 1, wherein heating is carried out for 30 minutes or longer.

3. The method according to claim 1, wherein the yield determined via thin-layer chromatography is 90% or higher in accordance with the formula: [molar quantity of starting material]/[molar quantity of β-hematin×2]×100.

4. The method according to claim 1, wherein in the β-hematin crystal produced, OH— or OH2 is bound to the sixth coordination position.

5. The method according to claim 1 wherein the β-hematin crystals have at least one of the structural features (i) to (v) below:
   (i) solid-state $^1$H-NMR analysis demonstrates main peaks at 6.8 ppm and -1.4 ppm;
   (ii) electron spin resonance (ESR) analysis at room temperature results in the detection of two apparent signals at around 0 to 200 mT (g=6.122) and at around 200 to 400 mT (g=2.005), ESR analysis at −50° C. results in the detection of a signal at around 0 to 100 mT that is stronger than a signal at around 200 to 300 mT, and ESR analysis at −150° C. results in the detection of a signal at around 0 to 100 mT that is at least twice as strong as a signal at around 200 to 300 mT;
   (iii) near-infrared spectroscopy does not result in the detection of peaks at 4440 cm$^{-1}$ 5780 cm$^{-1}$, and 5960 cm$^{-1}$;
   (iv) ultraviolet-visible spectroscopy results in the detection of peaks at 493 nm and 670 nm;
   (v) thermogravimetric/differential thermal analysis results in the detection of in the air, thermacogenesis at around 250° C. and rapid oxidative decomposition up to 400° C. and, in nitrogen, thermal decomposition involving endothermic changes at 360° C. and 440° C. and thermal decomposition involving thermacogenesis at around 700° C.

* * * * *